(12) United States Patent
Bergmann et al.

(10) Patent No.: US 7,560,231 B2
(45) Date of Patent: Jul. 14, 2009

(54) MANNITOL AND GLUCITOL DERIVATIVES

(75) Inventors: Frank Bergmann, Iffeldorf (DE);
Herbert Von Der Eltz, Weilheim (DE);
Christoph Seidel, Weilheim (DE); Kurt Weindel, Wielenbach-Hardt (DE)

(73) Assignee: Roche Molecular Systems, Inc., Pleasanton, CA (US)

( * ) Notice: Subject to any disclaimer, the term of this patent is extended or adjusted under 35 U.S.C. 154(b) by 563 days.

(21) Appl. No.: 10/729,570

(22) Filed: Dec. 5, 2003

(65) Prior Publication Data
US 2004/0157247 A1 Aug. 12, 2004

Related U.S. Application Data

(60) Provisional application No. 60/440,212, filed on Jan. 15, 2003.

(30) Foreign Application Priority Data

Dec. 20, 2002 (EP) ................. 02028714
Jan. 20, 2003 (EP) ................. 03001215

(51) Int. Cl.
  C12Q 1/68     (2006.01)
  C07H 21/00    (2006.01)
  C07F 9/06     (2006.01)
  C07D 327/00   (2006.01)
(52) U.S. Cl. .................. 435/6; 536/22.1; 536/25.3; 536/25.32; 546/22; 549/5
(58) Field of Classification Search .................. None
See application file for complete search history.

(56) References Cited

U.S. PATENT DOCUMENTS

| | | | |
|---|---|---|---|
| 4,458,066 A | 7/1984 | Caruthers et al. | 536/27 |
| 4,996,143 A | 2/1991 | Heller et al. | 435/6 |
| 5,130,238 A | 7/1992 | Malek et al. | 435/91 |
| 5,210,015 A | 5/1993 | Gelfand et al. | 435/6 |
| 5,451,463 A | 9/1995 | Nelson et al. | 428/402 |
| 5,478,972 A | 12/1995 | Mizutani et al. | 435/6 |
| 5,487,972 A | 1/1996 | Gelfand et al. | 435/6 |
| 5,565,322 A | 10/1996 | Heller | 435/6 |
| 5,607,922 A * | 3/1997 | De Clercq et al. | 514/43 |
| 5,659,023 A * | 8/1997 | Alexander et al. | 536/22.1 |
| 5,804,375 A | 9/1998 | Gelfand et al. | 435/6 |
| 5,849,489 A | 12/1998 | Heller | 435/6 |
| 6,103,476 A | 8/2000 | Tyagi et al. | 435/6 |
| 6,130,323 A | 10/2000 | Su et al. | 536/23.1 |
| 6,162,603 A | 12/2000 | Heller | 435/6 |
| 6,174,670 B1 | 1/2001 | Wittwer et al. | 435/6 |

FOREIGN PATENT DOCUMENTS

| | | |
|---|---|---|
| DE | 3943522 A1 | 2/1991 |
| EP | 0 439 182 B1 | 4/1996 |
| EP | 0 313 219 B1 | 5/1996 |
| EP | 1 186 613 A1 | 3/2002 |
| EP | 0 135 587 B2 | 12/2002 |
| WO | WO 90/01069 | 2/1990 |
| WO | WO 92/08808 | 5/1992 |
| WO | WO 93/25565 | 12/1993 |
| WO | WO 9521161 A1 * | 8/1995 |
| WO | WO 96/05213 | 2/1996 |
| WO | WO 96/41811 | 12/1996 |
| WO | WO 97/43451 | 11/1997 |
| WO | WO 9743451 A1 * | 11/1997 |
| WO | WO 99/09044 | 2/1999 |
| WO | WO 01/37291 A1 | 5/2001 |
| WO | WO 02/12263 A1 | 2/2002 |

OTHER PUBLICATIONS

Pravdić, N, et al., 1973, "Catalytic Hydrogenation of Some 2-Acetamidoaldose Derivatives", *Croatica Chemica ACTA*, 45:343-356.

Abramson, R., et al., 1993, "Nucleic Acid Amplification Technologies", *Current Opinion in Biotechnology*, 4:41-47.

Andersen, M., et al., 1996, "The Synthesis of Modified D- and L-Anhydrohexitol Nucleosides", *Tetrahedron Letters*, 37(45):8147-8150.

Barany, F., 1991, "Review: The Ligase Chain Reaction in a PCR World", *PCR Methods and Applications*, pp. 5-16.

Barany, F., 1991, "Genetic Disease detection and DNA amplification using cloned thermostable ligase", *Proc. Natl. Acad. Sci*, USA, 88:189-193.

Beaucage, S., et al., 1981, "Deoxynucleoside Phosphoramidites—a New Class of Key Intermediates for Deoxypolynucleotide Synthesis", *Tetrahedron Letters*, 22(20):1859-1862.

Brown, E., et al., 1979, "Chemical Synthesis and Cloning of a Tyrosine tRNA Gene", *Methods in Enzymology*, 68:109-151.

Garegg, P., et al., 1985, "Formation of Internucleotidic Bonds via Phosphonate Intermediates", *Chemical Scripta*, 25:280-282.

Gregrich, H., et al., 1998, "New Photolabile Protecting groups in Nucleoside and Nucleotide Chemistry—Synthesis, Cleavage Mechanisms and Applications", *Nucleosides and Nucleotides*, 17(9-11):1987-1996.

Gutelli, J., et al., 1990, "Isothermal, in vitro amplification of nucleic acids by a multienzyme reaction modeled after retroviral replication", *Proc. Natl. Acad. Sci*, USA, 87:1874-1878.

Hossain, N., et al., 1998, "Oligonucleotides Composed with 2'-Deoxy-1',5'-anhydro-D-mannitol Nucleosides with a Purine Base Moiety", *J. Org. Chem*, 63:1574-1582.

(Continued)

*Primary Examiner*—Janet L. Epps-Smith
(74) *Attorney, Agent, or Firm*—Olga Kay; Charles M. Doyle

(57) ABSTRACT

The present invention is related to compounds comprising mannitol or glucitol derivatives which may be used to build up oligomeric compounds. The invention is further related to uses of these oligomeric compounds for hybridization and as probes. In addition, methods for the detection of nucleic acids are disclosed wherein the oligomeric compounds are used.

28 Claims, 4 Drawing Sheets

OTHER PUBLICATIONS

Narang, S., et al., 1979, "Improved Phosphotriester method for the Synthesis of Gene Fragments", *Methods in Enzymology*, 68:90-98.

Jesús, M., et al., 1996, "Synthesis and Antiviral Activity of 2-Deoxy-1,5-Anhydro-D-Mannitol Nucleosides containing a pyrimidine base moiety", *Bioorganic & Medicinal Chemisty Letters*, 6(13):1457-1460.

Pravdić, N., et al., 1973, "Catalytic Hydrogenation of some 2-Acetamidoaldose Derivatives*", *Crotatica Chemica Acta*, 45:343:356.

Su, S., et al., 1997, "Novel Non-Nucleosidic Phosphoramidites for Oligonucleotide Modification and Labeling", *Bioorganic & Medicinal Chemistry Letters*, 7(13):1639-1644.

Uhlmann, E., et al., 1990, "Antisense Oligonucleotides: A new Therapeutic Principle", *Chemical Reviews*, 90(4):543-584.

Van Aerschot, A., et al., 1993, Synthesis of nucleoside analogues with a 1,5-anhydrohexitol moiety, *Bioorganic & Medicinal Chemistry Letters*, 3(60:1013-1018.

Verheggen, I., et al., 1993, "Synthesis and antiherpes Virus Activity of 1,5-anhydrohexitol nucleosides", *J Med. Chem.*, 36:2033-2040.

Verheggen, I., et al, 1995, Synthesis, biological evaluation and structure analysis of a series of new 1,5-anhydrohexitol nucleosides, *J Med. Chem.*, 38:826:835.

Verma, S., et al., 1998, "Modified Oligonucleotides: Synthesis and Strategy for Users", *Annu Rev. Boichem.*, 67:99-134.

Whelen, A., 1996, "The Role of Nucleic Acid Amplification and Detection in the Clinical Microbiology Laboratory[1]", *Annu Rev. Boichem.*, 50:349-373.

Wu, D., et al., 1989, "The Ligation Amplification Reaction (LAR)-Amplification of Specific DNA Sequences Using Sequential Rounds of Template-Dependent Ligation", *Genomics*, 4:560-569.

\* cited by examiner

| SEQ ID NO: | | | | Tm (heating) | Tm (cooling) |
|---|---|---|---|---|---|
| 1 | 5'- C A C C C C G T G C T | G C T G A C C G A | 3' | 73.5 | 75.1 |
| 2 | 3'- G T G G G G C A C G A | C G A C T G G C T C | C G G G 5' | | |
| 3 | 5'- C A C C C C G T G C T | G C T G A C C G A Flu | 3' | 72.3 | 74.5 |
| 4 | 3'- G T G G G G C A C G A | C G A C T G G C T C | C G G G 5' | | |
| 5 | 5'- C A C C C C G T G C Flu | G C T G A C C G A | 3' | 63.4 | 65.9 |
| 6 | 3'- G T G G G G C A C G A | C G A C T G G C T C | C G G G 5' | | |

Figure 4

MANNITOL AND GLUCITOL DERIVATIVES

This application claims the benefit of priority under 35 U.S.C. §119 of EP application No. 02028714.0, filed Dec. 20, 2002, U.S. Provisional Application No. 60/440,212 filed Jan. 15, 2003, and EP application No. 030012157.0 filed Jan. 20, 2003, the contents of which are hereby incorporated by reference.

BACKGROUND OF THE INVENTION

1. Field of the Invention

The present invention is related to compounds comprising mannitol or glucitol derivatives which may be used to build up oligomeric compounds. The invention is further related to uses of these oligomeric compounds for hybridization and as probes. In addition, methods for the detection of nucleic acids are disclosed wherein the oligomeric compounds are used.

2. Background of the Invention

In the field of molecular diagnostics, the detection of target nucleic acids with the polymerase chain reaction (PCR) plays an important role. The routine screening of blood banks for the presence of Human Immunodeficiency Virus (HIV), or Hepatitis-B (HBV) or C Virus (HCV) is an example for the large-scale application of PCR-based diagnostics. Automated systems for PCR-based analysis often make use of real-time detection of product amplification during the PCR process. Key to such methods is the use of modified oligonucleotides carrying reporter groups or labels.

In its simplest form, PCR is an in vitro method for the enzymatic synthesis of specific nucleic acid sequences, using two oligonucleotide primers that hybridise to opposite strands and flank the target sequence, that is the region of interest in the target nucleic acid. A repetitive series of reaction steps involving template denaturation, primer annealing, and the extension of the annealed primers by DNA polymerase (DNA: desoxyribonucleic acid) results in the exponential accumulation of a specific fragment whose termini are defined by the 5' ends of the primers. The detection of DNA amplification products generated by a PCR process can, on the one hand, be accomplished in separate working steps. These may involve the characterisation of amplified fragments with respect to their electrophoretic mobility and/or the analysis of denatured amplification products attached to a solid support using a hybridisation probe.

On the other hand, the detection of DNA amplification products can be done in a so-called "homogeneous" assay system. A "homogeneous" assay system comprises reporter molecules or labels which generate a signal while the target sequence is amplified. An example for a "homogeneous" assay system is the TaqMan® system that has been detailed in U.S. Pat. No. 5,210,015, U.S. Pat. No. 5,804,375 and U.S. Pat. No. 5,487,972. Briefly, the method is based on a double-labelled probe and the 5'-3' exonuclease activity of Taq DNA polymerase. The probe is complementary to the target sequence to be amplified by the PCR process and is located between the two PCR primers during each polymerisation cycle step. The probe has two fluorescent labels attached to it. One is a reporter dye, such as 6-carboxyfluorescein (FAM), which has its emission spectra quenched by energy transfer due to the spatial proximity of a second fluorescent dye, 6-carboxy-tetramethyl-rhodamine (TAMRA). In the course of each amplification cycle, the Taq DNA polymerase in the process of elongating a primed DNA strand displaces and degrades the annealed probe, the latter due to the intrinsic 5'-3' exonuclease activity of the polymerase. The mechanism also frees the reporter dye from the quenching activity of TAMRA. As a consequence, the fluorescent activity increases with an increase in cleavage of the probe, which is proportional to the amount of PCR product formed. Accordingly, amplified target sequence is measured detecting the intensity of released fluorescence label.

A similar principle of energy transfer between fluorescent dye molecules applies to "homogeneous" assays using so-called "molecular beacons" (U.S. Pat. No. 6,103,476). These are hairpin-shaped nucleic acid molecules with an internally quenched fluorophore whose fluorescence is restored when they bind to a target nucleic acid (U.S. Pat. No. 6,103,476). They are designed in such a way that the loop portion of the molecule is a probe sequence complementary to a region within the target sequence of the PCR process. The stem is formed by the annealing of complementary arm sequences on the ends of the probe sequence. A fluorescent moiety is attached to the end of one arm and a quenching moiety is attached to the end of the other arm. The stem keeps these two moieties in close proximity to each other, causing the fluorescence of the fluorophore to be quenched by energy transfer. Since the quencher moiety is a non-fluorescent chromophore and emits the energy that it receives from the fluorophore as heat, the probe is unable to fluoresce. When the probe encounters a target molecule, it forms a hybrid that is longer and more stable than the stem hybrid and its rigidity and length preclude the simultaneous existence of the stem hybrid. Thus, the molecular beacon undergoes a spontaneous conformational reorganisation that forces the stem apart, and causes the fluorophore and the quencher to move away from each other, leading to the restoration of fluorescence which can be detected.

More examples for "homogeneous" assay systems are provided by the formats used in the LightCycler® instrument (see e.g. U.S. Pat. No. 6,174,670), some of them sometimes called "kissing probe" formats. Again, the principle is based on two interacting dyes which, however, are characterised in that the emission wavelength of a donor-dye excites an acceptor-dye by fluorescence resonance energy transfer. An exemplified method uses two modified oligonucleotides as hybridisation probes, which hybridise to adjacent internal sequences of the target sequence of the PCR process. The 5'-located modified oligonucleotide has a donor-dye as a label at its 3' end. The 3'-located modified oligonucleotide has an acceptor-dye at its 5' end. Following the head-to-tail-oriented annealing of the two modified oligonucleotides to the target sequence in the course of an amplification cycle, donor and acceptor dye are brought in close proximity. Upon specific excitation of the donor dye by means of a monochromatic light pulse, acceptor dye fluorescence is detected providing a measure for the amount of PCR product formed.

The oligomeric compound or modified oligonucleotides used in "homogeneous" assay systems comprise nucleotides or modified nucleotides, i.e. the monomeric units, to which labels such as dyes as reporter molecules are attached. The features of such monomeric units are that they (1) can be attached to and/or integrated into the sugar-phosphate polymer backbone of a nucleic acid,
(2) do not prevent the pairing of the modified oligonucleotide with its complementary target sequence,
(3) provide functional groups for the attachment of one or more labels.

In addition, the TaqMan® format requires that the oligomeric compound can be digested by 5'-3' exonuclease activity of a template-dependent DNA-polymerase.

Several compounds and their use for incorporation as monomeric units into nucleic acids are known in the art. Such compounds provide functional groups and/or linking moieties for the covalent attachment of reporter groups or labels. In the course of the chemical synthesis of the oligomeric compound, the skeletal structure of the "non-nucleotide compound" or "modified nucleotide" is connected with the "oligonucleotide" backbone, for example by phosphoramidite-based chemistry resulting in a phosphodiester. A given incorporated compound thus represents a modified nucleotide within the newly generated "modified oligonucleotide". A label is bound by a functional group of a linking moiety, exemplified by but not limited to an amino function that is present on the skeletal structure proper or on the "linking moiety", which connects the skeleton with the functional group. A label can be covalently attached to the compound prior to the synthesis of a "modified oligonucleotide" or afterwards, upon the removal of an optional protecting group from the functional group to which the label is to be coupled.

EP 0135587 describes modifications of conventional nucleosides which carry a reporter group attached to a substituent group of the nucleotide base. EP 0313219 discloses non-nucleoside reagents characterised by a linear hydrocarbon skeletal structure with a linking moiety, or a side group to which a label can be bound. EP 0 313 219 is silent about other types of skeletal structures and their particular properties. U.S. Pat. No. 5,451,463 describes trifunctional non-nucleotide reagents, particularly 1,3-diol-based skeletal structures possessing a primary amino group. Such reagents can be used for example for terminal labelling of 3' termini of oligonucleotides. WO 97/43451 discloses non-nucleotide reagents based on a carbocyclic ($C_5$ to $C_7$) skeletal structure, whereby a substituted or unsubstituted cyclohexane is preferred. According to the document, such a structure provides rigidity which is necessary to extend a functional moiety, e.g. a functional group to which a reporter group can be coupled, away from the oligomeric backbone of the modified oligonucleotide. This is desired because the coupling efficiency of the reagent after the incorporation into a modified oligonucleotide is enhanced. Sheng-Hui, S., et al., Bioorganic & Medicinal Chem. Lett. 7 (1997) 1639-1644, describe non-nucleotide compounds based on a cyclohexane skeletal structure, particularly on the compound cyclohexyl-4-amino-1,1-dimethanol. The integration into the oligonucleotide backbone is made possible by functional groups substituting the methyl residues at the C1 position. To the amino group a linking moiety is attached which carries a label.

There are also disclosures with regard to glucitol or mannitol-based modified nucleosides. Compounds derived from 1,5-anhydro-2,3-dideoxy-hexitol are known to the art from several documents which, however, are focused on the hexitol compounds per se or on hexitol-based modified nucleosides. Such modified nucleosides can be used as drugs or for the purpose of chemical synthesis, particularly the synthesis of modified oligonucleotides. Pravdic, N., et al., Croatica Chemica Acta 45 (1973) 343-356, describe the synthesis of 1,5-anhydro-2-acetamido-2,3-dideoxy-D-hexitol, i.e. the -mannitol or -glucitol derivative (compound XVIII). The document is, completely silent about particular uses of such compounds, other than for chemical synthesis. JP 60016982 describes the synthesis of 1,5-anhydro-3-deoxy-D-glucitol. The compound is described for the use of suppressing the activity of glucose-acceptive neurons. WO 93/25565, van Aerschot, A., et al., Bioorganic & Medicinal Chemistry Letters (1993) 1013-1018; Verheggen, I., et al., J. Med. Chem. 36 (1993) 2033-2040; Verheggen, I., et al., J. Med. Chem. 38 (1995) 826-835; and Perez-Perez, M.-J., et al., Bioorg. & Med. Chem. Lett. 6 (1996) 1457-1460, describe 1,5-anhydro-2,3-dideoxy-D-hexitol derivatives that carry at the C2 position a hydroxyl residue or a heterocyclic base. Andersen, M. W., et al., Tetrahedron Lett. 37 (1996) 8147-8150 describe similar modified nucleosides; however, the authors also mention 1,5-anhydro-2,3-dideoxy-D-hexitol derivatives that carry at the C2 position a hydroxyl residue or an amino residue. WO 9605213 and Hossain, N., et al., J. Org. Chem. 63 (1998) 1574-1582 describe the synthesis of modified nucleosides derived from 1,5-anhydro-2,3-dideoxy-D-glucitol and -mannitol, respectively. The latter two documents disclose the synthesis of modified oligonucleotides having incorporated hexitol-based modified nucleosides.

Compounds to be used for the incorporation of labels into nucleic acids have to be carefully selected as they may:
(a) interfere with base pairing,
(b) fail to provide a skeletal structure of sufficient rigidity,
(c) provide largely hydrophobic structures resulting in low water solubility,
(d) provide only limited amenability to chemical modifications,
(e) comprise mixtures of enantiomers Therefore, it was an object of the present invention to provide new compounds to be used for the incorporation of labels into nucleic acids.

SUMMARY OF THE INVENTION

The present invention is related to compounds comprising mannitol or glucitol moieties, in particular specific compounds comprising mannitol or glucitol moieties which may be used to build up oligomeric compounds. The invention is further related to uses of these oligomeric compounds for hybridization and as probes. In addition, methods for the detection of a nucleic acid in a sample are disclosed wherein the oligomeric compounds are used. Further, a method for the separate and direct synthesis of the -mannitol and -glucitol stereoisomers is provided, thus obviating the need to separate mixtures of the two.

The 1,5-anhydro-2-amino-2,3-dideoxy-hexitol structure provides as a particularly advantageous property a hydrophilic skeletal structure. Moreover, the hexitol structure is amenable to further efficient chemical synthesis. For instance, as mannitol or glucitol structures have only a singular primary alcoholic function, selective coupling of a DMT protecting group to the hydroxyl oxygen at the hexitol 6 carbon atom can be done in an efficient way. The chemical synthesis of the compounds according to the invention constitutes with particular respect to the 2-amino group, a particular advantage as the synthetic steps are suited to generate selectively either of the two possible stereoisomers. Thus, elaborate separation steps can be avoided and at the same time defined compounds are obtained which is an advantage for the production of compounds for diagnostic use where high quality standards are needed, i.e. also defined products and not enantiomers, not neglecting aspects of the production costs. In case a fluorescent label is coupled to the 2-amino group, mannitol- or glucitol-based compounds, when incorporated into a nucleic acid or a modified nucleic acid, provide the structural basis for a 5'- or 3'-directed orientation of the label.

Conventional techniques of molecular biology and nucleic acid chemistry, which are within the skill of the art, are explained in the literature. See, for example, Sambrook et al., Molecular Cloning: A Laboratory Manual, Cold Spring Harbor Laboratory, Cold Spring Harbor, N.Y., 1989; Oligonucleotide Synthesis, Gait, M. J., ed., 1984; Nucleic Acid Hybridization, Hames, B. D., and Higgins, S. J., eds., 1984; and a series, Methods in Enzymology, Academic Press, Inc., all of which are incorporated herein by reference. All patents, patent applications, and publications mentioned herein, both supra and infra, are incorporated herein by reference.

As is known in the art, a "nucleoside" is a base-sugar combination. The base portion of the nucleoside is normally a heterocyclic base. The two most common classes of such heterocyclic bases are the purines and the pyrimidines.

"Nucleotides" are "nucleosides" that further include a phosphate group covalently linked to the sugar portion of the nucleoside. For those "nucleosides" that include a pentofuranosyl sugar, the phosphate group can be linked to either the 2', 3' or 5' hydroxyl moiety of the sugar. A "nucleotide" is the "monomeric unit" of an "oligonucleotide", more generally denoted herein as an "oligomeric compound", or a "polynucleotide", more generally denoted as a "polymeric compound". Another general expression therefor is desoxyribonucleic acid (DNA) and ribonucleic acid (RNA).

"Modified nucleotides" (or "nucleotide analogs") differ from a natural "nucleotide" by some modification but still consist of a base, a pentofuranosyl sugar, a phosphate portion, base-like, pentofuranosyl sugar-like and phosphate-like portion or combinations thereof. For example, a "label" may be attached to the base portion of a "nucleotide" whereby a "modified nucleotide" is obtained. A natural base in a "nucleotide" may also be replaced by e.g. a 7-desazapurine whereby a "modified nucleotide" is obtained as well. The terms "modified nucleotide" or "nucleotide analog" are used interchangeably in the present application. A "modified nucleoside" (or "nucleoside analog") differs from a natural nucleoside by some modification in the manner as outlined above for a "modified nucleotide" (or a "nucleotide analog").

A "non-nucleotide compound" is different from a natural "nucleotide" but is in the sense of this invention still capable—similar to a "nucleotide"—of being a "monomeric unit" of an "oligomeric compound". Therefore, a "non-nucleotide compound" has to be capable of forming an "oligomeric compound" with "nucleotides". Even "non-nucleotide compounds" may contain a base-like, pentofuranosyl sugar-like or a phosphate-like portions, however, not all of them are present at the same time in a "non-nucleotide compound".

According to the invention, an "oligomeric compound" is a compound consisting of "monomeric units" which may be "nucleotides" alone or "non-natural compounds", more specifically "modified nucleotides" (or "nucleotide analogs") or "non-nucleotide compounds", alone or combinations thereof. "Oligonucleotides" and "modified oligonucleotides" (or "oligonucleotide analogs") are subgroups of "oligomeric compounds" in the context of the invention.

In the context of this invention, the term "oligonucleotide" refers to "polynucleotides" formed from a plurality of "nucleotides" as the "monomeric unit", i.e. an "oligonucleotide" belongs to a specific subgroup of a "oligomeric compound" or "polymeric compound" of ribonucleic acid (RNA) or deoxyribonucleic acid (DNA) with "monomeric units". According to this invention, the term "oligonucleotide" only includes "oligonucleotides" composed of naturally-occurring "nucleotides". The phosphate groups are commonly referred to as forming the internucleoside backbone of the "oligonucleotide". The normal linkage or backbone of RNA and DNA is a 3' to 5' phosphodiester linkage.

A "modified oligonucleotide" (or "oligonucleotide analog") belongs to another specific subgroup of the "oligomeric compounds", that possesses one or more "nucleotides", one or more "non-nucleotide compounds" or "modified nucleotides" as "monomeric units". Thus, the terms "modified oligonucleotide" (or "oligonucleotide analog") refers to structures that function in a manner substantially similar to "oligonucleotides" and are used interchangeably throughout the application. From a synthetical point of view, a "modified oligonucleotide" (or a "oligonucleotide analog") can be for example made by chemical modification of "oligonucleotides" by appropriate modification of the phosphate backbone, ribose unit or the nucleotide bases (Uhlmann and Peyman, Chemical Reviews 90 (1990) 543; Verma, S., and Eckstein, F., Annu. Rev. Biochem. 67 (1998) 99-134). Representative modifications include phosphorothioate, phosphorodithioate, methyl phosphonate, phosphotriester or phosphoramidate inter-nucleoside linkages in place of phosphodiester inter-nucleoside linkages; deaza or aza purines and pyrimidines in place of natural purine and pyrimidine bases, pyrimidine bases having substituent groups at the 5 or 6 position; purine bases having altered substituent groups at the 2, 6 or 8 positions or 7 position as 7-deazapurines; sugars having substituent groups at, for example, their 2' position; or carbocyclic or acyclic sugar analogs. Other modifications consistent with the spirit of this invention are known to those skilled in the art. Such "modified oligonucleotides" (or "oligonucleotide analogs") are best described as being functionally interchangeable with, yet structurally different from, natural "oligonucleotides" (or synthetic "oligonucleotides" along natural lines). In more detail, exemplary modifications are disclosed in Verma, S., and Eckstein, F., Annu. Rev. Biochem. 67 (1998) 99-134 or WO 02/12263. In addition, modification can be made wherein nucleoside units are joined through groups that substitute for the internucleoside phosphate or sugar phosphate linkages. Such linkages include those disclosed in Verma, S., and Eckstein, F., Annu. Rev. Biochem. 67 (1998) 99-134. When other than phosphate linkages are utilized to link the nucleoside units, such structures have also been described as "oligonucleosides".

"Oligomeric compounds" as "oligonucleotides" and "modified oligonucleotides" according to the invention may be synthesized as principally described in the art and known to the expert in the field. Methods for preparing oligomeric compounds of specific sequences are known in the art, and include, for example, cloning and restriction of appropriate sequences and direct chemical synthesis. Chemical synthesis methods may include, for example, the phosphotriester method described by Narang, S. A., et al., Methods in Enzymology 68 (1979) 90-98, the phosphodiester method disclosed by Brown, E. L., et al., Methods in Enzymology 68 (1979)109-151, the phosphoramidite method disclosed in Beaucage et al., Tetrahedron Letters 22 (1981) 1859, the H-phosphonate method disclosed in Garegg, et al., Chem. Scr. 25 (1985) 280-282 and the solid support method disclosed in U.S. Pat. No. 4,458,066.

As said above, a "nucleic acid" is a polymeric compound of "nucleotides" as known to the expert skilled in the art. It is used herein to denote a "nucleic acid" in a sample which should be analyzed, i.e. the presence, non-presence or amount thereof in a sample should be determined. Therefore, in other words the "nucleic acid" is the target and can therefore be also denoted as "target nucleic acid". For example, if it has to be determined whether blood contains the human immunodeficiency virus, the "target nucleic acid" is the nucleic acid of the human immunodeficiency virus.

The term "primer" is used herein as known to the expert skilled in the art and refers to "oligomeric compounds" primarily to "oligonucleotides" but also to "modified oligonucleotides" that are able to "prime" DNA synthesis by a template-dependent DNA polymerase, i.e. the 3'-end of the e.g. oligonucleotide provides a free 3'-OH group whereto further "nucleotides" may be attached by a template-dependent DNA polymerase establishing 3' to 5' phosphodiester linkage whereby desoxynucleoside triphosphates are used and whereby pyrophosphate is released.

The term "probe" refers to synthetically or biologically produced nucleic acids (DNA or RNA) which, by design or selection, contain specific nucleotide sequences that allow them to hybridize under defined predetermined stringencies specifically (i.e., preferentially) to "target nucleic acids". A "probe" can be identified as a "capture probe" meaning that it "captures" the target nucleic acid so that it can be separated from undesirable materials which might obscure its detection. Once separation is accomplished, detection of the captured "target nucleic acid" can be achieved using a suitable procedure. "Capture probes" are often already attached to a solid phase.

"Alkyl" groups are preferably chosen from alkyl groups containing from 1 to 10 carbon atoms, either arranged in linear, branched or cyclic form. The actual length of the alkyl group will depend on the steric situation at the specific position where the alkyl group is located. If there are steric constraints, the alkyl group will generally be smaller, the methyl and ethyl group being most preferred. All alkyl, alkenyl and alkynyl groups can be either unsubstituted or substituted. Substitution by hetero atoms as outlined above, will help to increase solubility in aqueous solutions.

"Alkenyl" groups are preferably selected from alkenyl groups containing from 2 to 10 carbon atoms. For the selections similar considerations apply as for alkyl groups. They also can be linear, branched and cyclic. The most preferred alkenyl group is the ethylene group. There can be more than one double bond in the alkenyl group.

"Alkynyl" groups have preferably from 2 to 10 carbon atoms. Again, those carbon atoms can be arranged in linear, branched and cyclic manner. There can be more than one triple bond in the alkynyl group.

A "protecting group" is a chemical group that is attached to a functional moiety (for example to the oxygen in a hydroxyl group, the nitrogen in an amino group or the sulfur in a thiol group, thereby replacing the hydrogen) to protect the functional group from reacting in an undesired way. A protecting group is further defined by the fact that it can be removed without destroying the biological activity of the molecule formed, here the binding of the nucleic acid binding compound to a nucleic acid. Suitable protecting groups are known to a man skilled in the art. Preferred protecting groups according to this invention are fluorenylmethoxycarbonyl (FMOC), dimethoxytrityl-(DMT), monomethoxytrityl-, trifluoroacetyl-, levulinyl-, or silyl-groups. Preferred protecting groups for example for hydroxyl groups at the 5'-end of a nucleotide or oligonucleotide are selected-, from the trityl groups, for example dimethoxytrityl (DMT). Preferred protecting groups at exocyclic amino groups in formula I are acyl groups, most preferred the benzoyl group (Bz), phenoxyacetyl or acetyl or formyl, and the amidine protecting groups as e.g. the N,N-dialkylformamidine group, preferentially the dimethyl-, diisobutyl-, and the di-n-butylformamidine group. Preferred O-protecting groups are the aroyl groups, the diphenylcarbamoyl group, the acyl groups, and the silyl groups. Among these most preferred is the benzoyl group. Preferred silyl groups are the trialkylsilyl groups, like, trimethylsilyl, triethylsilyl and tertiary butyl-dimethyl-silyl. Another preferred silyl group is the trimethylsilyl-oxy-methyl group (TOM)(WO99/09044). Further, preferred protecting groups are ortho nitro-benzyl, 2-(4-nitrophenyl)ethoxycarbonyl (NPEOC), photoactivable compounds as 2-nitrophenyl-propyloxy-carbonyl (NPPOC) (Giegrich et al., Nucleosides & Nucleotides17 (1998) 1987) and allyloxycarbonyl.

"Labels", often referred to as "reporter groups", are generally groups that make a nucleic acid, in particular the "oligomeric compound" or the "modified oligonucleotide" according to the invention, as well as any nucleic acids bound thereto distinguishable from the remainder of the liquid, i.e. the sample (nucleic acids having attached a "label" can also be termed labeled nucleic acid binding compounds, labeled probes or just probes). Preferred labels according to the invention are fluorescent labels, which are e.g. fluorescent dyes as a fluorescein dye, a rhodamine dye, a cyanine dye, and a coumarin dye.

The term "linking moiety" refers to a group of atoms which connect the moiety intended to be used (e.g. the "solid phase" or the "label") to the position of attachment at the "nucleotide", "modified nucleotide" or "non-nucleotide compound". This can be e.g. the base, sugar or phosphate moiety of a "nucleotide" or "modified nucleotide" (or under special circumstances even for a "non-nucleotide compound") or the base-like, sugar-like or phosphate-like moiety of a "non-nucleotide compound" or "modified nucleotide". The "linking moiety" will provide flexibility such that the "oligomeric compound" according to the invention, in particular the "modified oligonucleotide", can bind the "target nucleic acid" to be determined without major hindrance by the "solid phase" or "label". "Linking moieties", especially those that are not hydrophobic, for example based on consecutive ethylenoxy-units, for example as disclosed in DE 3943522 are known to an expert skilled in the art.

According to the invention, a "solid phase" may be controlled pore glass (CPG), polystyrene or silica gel as used for oligonucleotide synthesis. As used herein, "fluorescence resonance energy transfer relationship" and similar terms refer to adjacent hybridization of an "oligomeric compound" labeled with a "donor fluorescent label" and another "oligomeric compound" labeled with an "acceptor fluorescent label" to a "target nucleic acid" such that the "donor fluorescent label" can transfer resonance energy to the "acceptor fluorescent label" such that the "acceptor fluorescent label" produces a measurable fluorescence emission. If the "donor fluorescent label" and "acceptor fluorescent label" are spaced apart by too great a distance, then the "donor fluorescent label" cannot transfer resonance energy to the "acceptor fluorescent label" such that the "acceptor fluorescent label" emits measurable fluorescence, and hence the "donor fluorescent label" and "acceptor fluorescent label" are not in resonance energy transfer relationship.

By "array" is meant an arrangement of addressable locations on a device (see e.g. U.S. Pat. No. 5,143,854, U.S. Pat. No. 6,022,963, U.S. Pat. No. 6,156,501, WO90/15070, WO 92/10092). The locations can be arranged in two dimensional arrays, three dimensional arrays, or other matrix formats. The number of locations can range from several to at least hundreds of thousands. Most importantly, each location represents a totally independent reaction site. Each location carries a nucleic acid as e.g. an "oligomeric compound", which can serve as a binding partner for a second nucleic acid, in particular a target nucleic acid.

DESCRIPTION OF THE FIGURES

FIG. 4: Hybridization experiments with modified oligonucleotides having incorporated a FAM residue via a hexitol derived compound according to the invention (Flu=FAM-Mannitol compound according to the invention whereby FAM stands for fluorescein attached via a linking moiety to the mannitol moiety).

DETAILED DESCRIPTION OF THE INVENTION

Figure 1:
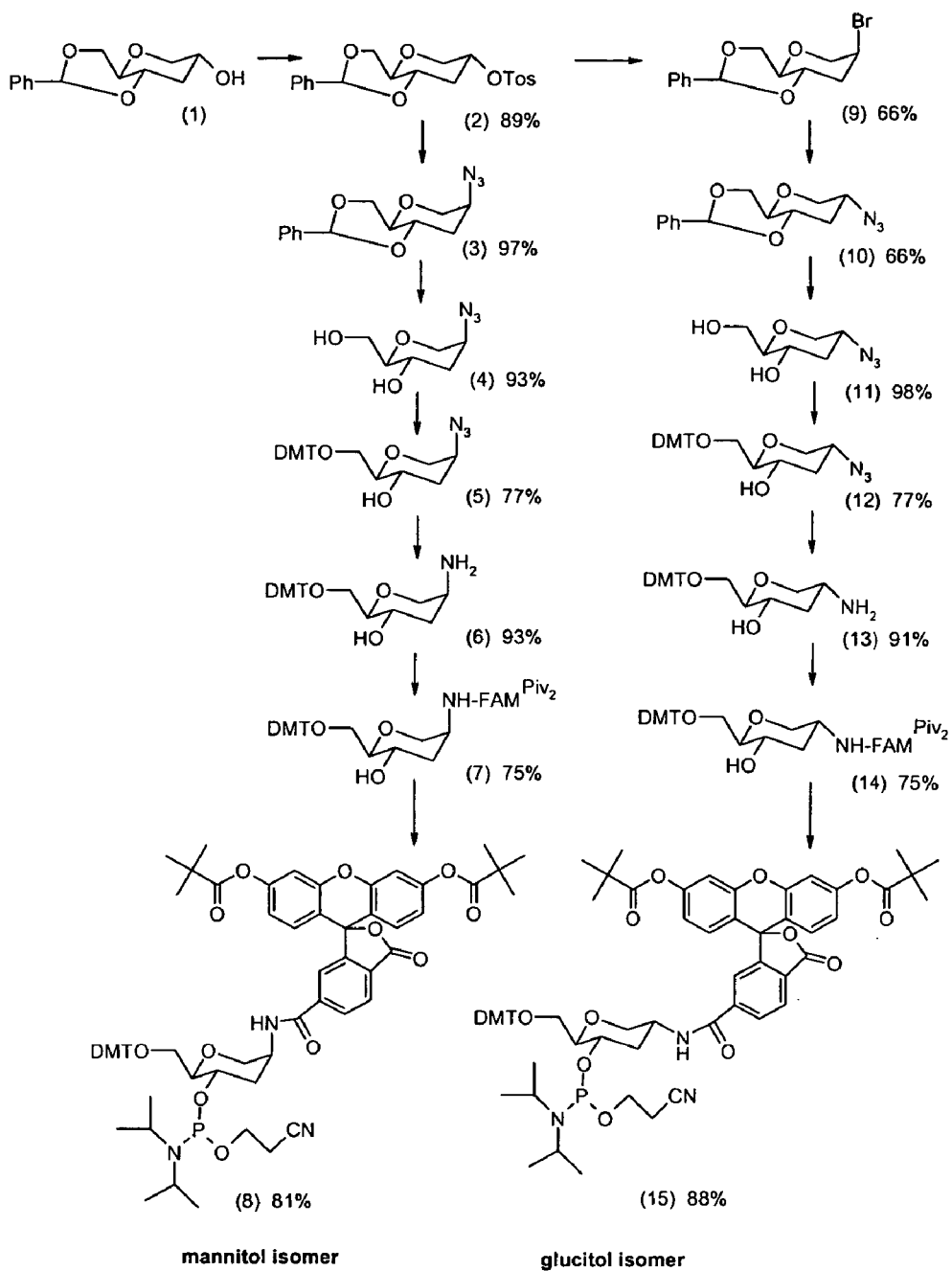
FIG. 1: Synthesis of fluorescein labelled phosphoramidites based on 1,5-anhydro-3-deoxy-D-mannitol (8) and glucitol (15).

In an embodiment of the invention a compound of the formula I is provided

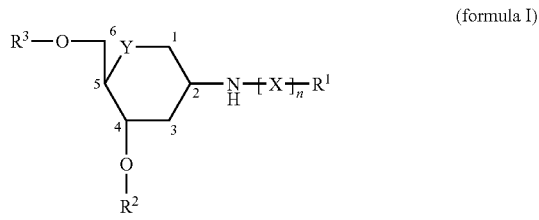

(formula I)

wherein Y is selected from the group consisting of O, S, and $NR^4$, whereby $R^4$ is alkyl-, alkenyl, alkinyl, aryl-, acyl-, a protecting group or H, wherein X is a linking moiety whereby n is 0 or 1, wherein $R^1$ is independent from $R^2$, $R^3$ and $R^4$, and wherein $R^1$ is selected from the group consisting of
(1) a protecting group,
(2) a label, and
(3) a solid phase, wherein $R^2$ and $R^3$ are independent from each other and independent from $R^1$ or $R^4$, and wherein $R^2$ and $R^3$ are selected from the group consisting of
(1) —H,
(2) a protecting group,
(3) a solid phase and a linking moiety X,
(4) a phosphoramidite,
(5) a H-phosphonate, and
(6) a triphosphate, with the proviso that $R^3$ but not $R^2$ can be triphosphate and $R^1$ is not a solid phase if $R^3$ is a triphosphate, with the proviso that $R^2$ and $R^3$ are not both a solid phase, not both a phosphoramidite, not both a H-phosphonate, not both —H or not both a protecting group, or not a phosphoramidite and a H-phosphonate, or not a solid phase and a phosphoramidite, or not a solid phase and a H-phosphonate, and with the proviso that when one residue selected from the group consisting of $R^1$, $R^2$ or $R^3$ is a solid phase then the other two residues selected from the group consisting of $R^1$, $R^2$ or $R^3$ are not a solid phase.

In the most preferred embodiment, Y is O.

In another preferred embodiment, $R^1$ is independent from $R^2$, $R^3$ and $R^4$, and $R^1$ is selected from a protecting group and a label, whereby it is most preferred that $R^1$ is a label.

Particularly preferred according to the invention are compounds useful for the synthesis of oligomeric compounds according to the invention. Therefore, in a preferred embodiment, $R^2$ and $R^3$ are independent from each other and independent from $R^1$ or $R^4$, and $R^2$ is selected from the group consisting of a solid phase and a linking moiety X, a phosphoramidite, and a H-phosphonate and wherein $R^3$ is —H or a protecting group, preferably $R^3$ is a protecting group. In an even more preferred embodiment, $R^2$ and $R^3$ are independent from each other and independent from $R^1$ or $R^4$, and $R^2$ is a solid phase and a linking moiety X and $R^3$ is —H. In another even more preferred embodiment, $R^2$ and $R^3$ are independent from each other and independent from $R^1$ or $R^4$, and $R^2$ is a phosphoramidite or a H-phosphonate, preferably $R^2$ is a phosphoramidite, and $R^3$ is a protecting group, whereby $R^1$ is a label or a protecting group, whereby preferably $R^1$ is a label. In this case, it is preferred that X is a linking moiety whereby n is 1.

In a preferred embodiment of the invention, X is a linking moiety whereby n is 1. In another preferred embodiment, the linking moiety X of the compound according to the invention comprises carbon and oxygen atoms. In a more preferred embodiment, the linking moiety X comprises —$(CH_2)_m$— or —$(CH_2CH_2O)_m$— moieties whereby m is an integer number between 0 and 10, preferably between 1 and 10. In an even more preferred embodiment, the linking moiety X is selected from the group consisting of (1) —CO—$(CH_2)_m$-Z-
(2) —CO—$(CH_2CH_2O)_m$—$CH_2CH_2$-Z- whereby m is an integer number between 0 and 10, preferably between 1 and 10, and whereby Z is selected from the group consisting of NH, CO, O and S. In a very preferred embodiment of the invention, Z is NH or CO. In an embodiment, the linker is a oxalyl derivative, i.e. X is —CO—CO— which means that Z=CO and m=0 in —CO—$(CH_2)_m$-Z-. However, more preferably, m is 2 or 3. Therefore most preferred, the linker is a succinic acid derivative, i.e. X is —CO—$(CH_2)_2$—CO— which means that Z=CO and m=2 in —CO—$(CH_2)_m$-Z-. In another preferred embodiment, the linker is a glutaric acid derivative, i.e. X is —CO—$(CH_2)_3$—CO— which means that Z=CO and m=3 in —CO—$(CH_2)_m$-Z.

In a preferred embodiment of the invention, the protecting group is selected from the group consisting of
fluorenylmethoxycarbonyl-,
dimethoxytrityl-,
monomethoxytrityl-,
trifluoroacetyl-,
levulinyl-, and
silyl-.

In a preferred embodiment of the invention, the $R^1$ is a label, preferably a fluorescent label as a fluorescent dye selected from the group consisting of
a fluorescein dye,
a rhodamine dye,
a cyanine dye, and
a coumarin dye.

In another preferred embodiment of the invention, the compound is a derivative of 1,5-anhydro-2-amino-2,3-dideoxy-D-glucitol with the formula as depicted below

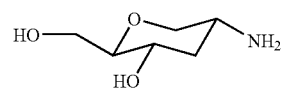

or 1,5-anhydro-2-amino-2,3-dideoxy-D-mannitol with the formula as depicted below

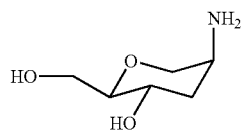

A particularly preferred embodiment of the invention is a compound, a glucitol-FAM-phosphoramidite, with the formula

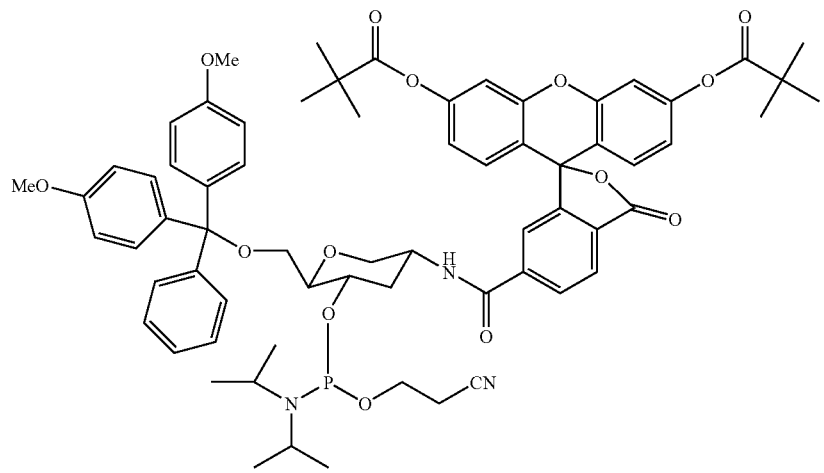

Another particularly preferred embodiment of the invention is a compound, a mannitol-FAM-phosphoramidite, with the formula

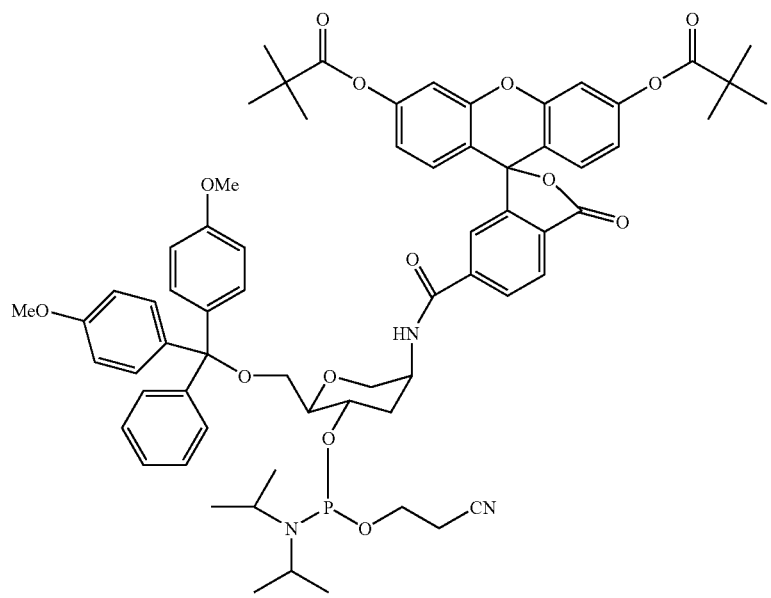

Another particularly preferred embodiment of the invention is a compound with the formula (FMOC: 9-fluorenyl-methoxycarbonyl as protecting group)

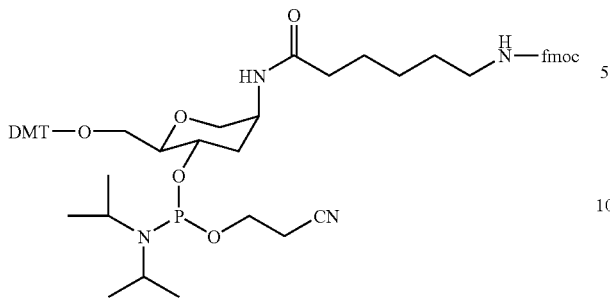

In a very preferred embodiment of the invention, an oligomeric compound is provided comprising a monomeric unit with formula II:

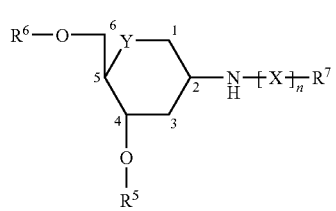

(formula II)

wherein Y is selected from the group consisting of O, S and $NR^4$, whereby $R^4$ is alkyl-, alkenyl, alkinyl, aryl-, acyl-, a protecting group or H;

wherein X is a linking moiety whereby n is 0 or 1;

wherein $R^7$ is independent from $R^4$, $R^5$ and $R^6$ and wherein $R^7$ is selected from the group consisting of
(1) —H,
(2) a protecting group,
(3) a label,
(4) an oligonucleotide, and
(5) a solid phase, wherein $R^5$ and $R^6$ are independent from each other and independent from $R^4$ or $R^7$, and wherein $R^5$ and $R^6$ are selected from the group consisting of
(1) —H,
(2) a solid phase and a linking moiety X,
(3) a phosphate, and
(4) a phosphodiester with a nucleotide, a modified nucleotide, an oligonucleotide or a modified oligonucleotide, with the proviso that $R^5$ and $R^6$ are not both —H, both a solid phase and a linking moiety X, both a phosphate, or —H and a phosphate, with the proviso that when one residue selected from the group consisting of $R^5$, $R^6$ or $R^7$ is a solid phase then the other residues selected from the group consisting of $R^5$, $R^6$ or $R^7$ are not a solid phase.

In a preferred embodiment Y is O.

In another preferred embodiment of the invention, the monomeric unit is a derivative of 1,5-anhydro-2-amino-2,3-dideoxy-D-glucitol with the formula as depicted below

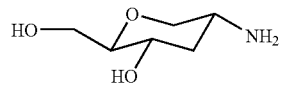

or 1,5-anhydro-2-amino-2,3-dideoxy-D-mannitol with the formula as depicted below

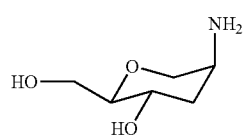

In another preferred embodiment, $R^7$ is independent from $R^4$, $R^5$ and $R^6$, and $R^7$ is selected from the group consisting of —H, a solid phase, a protecting group and a label, whereby it is most preferred that $R^7$ is a —H or label, whereby it is more preferred that $R^7$ is a label.

In another preferred embodiment, $R^5$ and $R^6$ are independent from each other and independent from $R^7$ or $R^4$, and $R^5$ and $R^6$ are selected from the group consisting of —H, a phosphate, and a phosphodiester with an oligonucleotide or a modified oligonucleotide. In another preferred embodiment, $R^5$ and $R^6$ are independent from each other and independent from $R^4$ or $R^7$, and $R^5$ and $R^6$ are a phosphodiester with a an oligonucleotide or a modified oligonucleotide.

In a preferred embodiment of the invention, X is a linking moiety whereby n is 1. In another preferred embodiment, the linking moiety X of the oligomeric compound according to the invention comprises carbon and oxygen atoms. In a more preferred embodiment, the linking moiety X comprises $—(CH_2)_m$ or $—(CH_2CH_2O)_m$ moieties whereby m is an integer number between 0 and 10, preferably between 1 and 10. In an even more preferred embodiment, the linking moiety X is selected from the group consisting of
(1) —CO—$(CH_2)_m$-Z-
(2) —CO—$(CH_2CH_2O)_m$—$CH_2CH_2$-Z- whereby m is an integer number between 0 and 10, preferably between 1 and 10, and whereby Z is selected from the group consisting of NH, CO, O and S. In a very preferred embodiment of the invention, Z is NH or CO. In an embodiment, the linker is a oxalyl derivative, i.e. X is —CO—CO— which means that Z=CO and m=0 in —CO—$(CH_2)_m$-Z-. However, more preferably, m is 2 or 3. Therefore most preferred, the linker is a succinic acid derivative, i.e. X is —CO—$(CH_2)_2$—CO— which means that Z=CO and m=2 in —CO—$(CH_2)_m$-Z-. In another preferred embodiment, the linker is a glutaric acid derivative, i.e. X is —CO—$(CH_2)_3$—CO— which means that Z=CO and m=3 in —CO—$(CH_2)_m$-Z-.

In a preferred embodiment, the protecting group of the oligomeric compound according to the invention is selected from the group consisting of
(1) fluorenylmethoxycarbonyl-,
(2) dimethoxytrityl-,
(3) monomethoxytrityl-,
(4) trifluoroacetyl-,
(5) levulinyl-, or
(6) silyl-.

In another preferred embodiment of the invention, $R^7$ of the oligomeric compound according to the invention is a label, preferably a fluorescent label (or fluorescent dye), preferably selected from the group consisting of (1) a fluorescein dye,
(2) a rhodamine dye,
(3) a cyanine dye, and
(4) a coumarin dye.

The most preferred fluorescent label is a fluorescein or a rhodamine dye. In another preferred embodiment of the invention, the oligomeric compound according to the invention comprises a monomeric unit that is
(1) a second label, preferably second fluorescent label, more preferably a linking moiety with a second fluorescent label, attached to the base, sugar or phosphate moiety of a nucleotide, or
(2) a second label, preferably a second fluorescent label, more preferably a linking moiety with a second fluorescent label, attached to a modified nucleotide or non-nucleotide compound.

The second fluorescent label is preferably a fluorescein dye, a rhodamine dye, a cyanine dye, or a coumarin dye. The most preferred second fluorescent label is a rhodamine or a cyanine dye.

Only in the case of the existence of a second label or fluorescent label, the label or fluorescent label may also be denoted as a first label or first fluorescent label for the sake of clarity.

In another preferred embodiment of the invention, the oligomeric compound according to the invention comprises a monomeric unit that is
(1) a protected linking moiety attached to the base, sugar or phosphate moiety of a nucleotide
(2) a linking moiety with a protecting group attached to a modified nucleotide or non-nucleotide compound.

In another embodiment of the invention, the modified oligonucleotide of the oligomeric compound according to the invention comprises a monomeric unit that comprises a moiety selected from the group consisting of
(1) cyclohexane-1,1-dimethanol (as described in U.S. Pat. No. 6,130,323),
(2) 1,3-propanediol (as described in U.S. Pat. No. 5,451,463),
(3) 2,2-di-(3-aminopropyl)-1,3-dihydroxypropane (as described in EP 0313 219), and
(4) 1,5-anhydro-2-amino-2,3-dideoxy-hexitol.

Preferably, the modified oligonucleotide of the oligomeric compound according to the invention comprises a monomeric unit that comprises a 1,5-anhydro-2-amino-2,3-dideoxy-hexitol moiety according to the invention.

For use in the formats used in the LightCycler® Instrument, the compound according to the invention will be preferably directed to the 3'- or 5'-end of the oligomeric compound during the synthesis thereof.

Preferably for use in the TaqMan® format, the label $R^7$ attached to the oligomeric compound according to the invention may be located after synthesis internally in the oligomeric compound according to the invention, at the 5'-end or the 3'-end of the oligomeric compound according to the invention. The label is preferably a fluorescent label, preferably a fluorescein or a rhodamine dye. The oligomeric compound according to the invention may further comprise other labels wherein the emission wavelengths of one of the labels overlaps the absorption wavelengths of another of the labels. Preferably, the oligomeric compound further comprises a second label acting as a quenching agent, that quenches the fluorescence emission of the fluorescent label, which can be fluorescein. Preferably the quenching agent is a fluorescent rhodamine or cyanine dye or a non-fluorescent label as dabcyl ("Dark quencher").

In the most preferred embodiment, the oligomeric compound according to the invention cannot be extended enzymatically to be used as probe in the TaqMan® format as principally set out in U.S. Pat. No. 5,210,015, U.S. Pat. No. 5,478,972 or U.S. Pat. No. 5,804,375. Preferably, the monomeric unit at the 3'-end of the oligomeric compound is a 2',3'-dideoxynucleotide or a 3'-phosphorylated nucleotide. Preferably for use in the TaqMan® format, the monomeric unit according to the invention with a label, preferably a fluorescent label, as well as a second monomeric unit with another label, preferably a second fluorescent label, may be located internally in the oligomeric compound according to the invention or at the 5'-end and/or 3'-end of the oligomeric compound according to the invention.

The expert skilled in the art acknowledges the fact that the hexitol ring of the compound according to the invention or of the oligomeric compound according to the invention may carry further substituents and still be functional in the methods according to the invention. In particular the hexitol but also the linking moiety may carry further halogen or alkyl, alkenyl, alkynyl, aryl optionally containing heteroatoms or heteroaryl substitutents optionally substituted with further substituents as already denoted. These compounds may be tested whether they can be used in the methods or uses according to the invention by e.g. simple hybridization experiments with complementary oligonucleotides as described under 1.5., in the assay formats used in the LightCycler® instrument or in the TaqMan® instrument or in the chemical synthesis method according to the invention making use of phosphoramidite or solid phase-linked compounds.

In a further embodiment, the compound according to the invention, wherein $R^2$ is phosphoramidite or a solid phase with a linking moiety X and $R^3$ is a protecting group, is used for the chemical synthesis of a modified oligonucleotide according to the invention. In another embodiment, the oligomeric compound according to the invention is used in a hybridisation reaction with a nucleic acid. This can be also done in a so-called array format. In another embodiment of the invention, the oligomeric compound according to the invention is used as a primer, probe or capture probe.

The oligomeric compounds according to the invention may be synthesized as principally described in the art and known to the expert in the field, particularly preferred building blocks therefor are the compounds according to the invention. Methods for preparing oligomeric compounds as oligonucleotides and modified oligonucleotides of specific sequences are known in the art, and include, for example, cloning and restriction of appropriate sequences and direct chemical synthesis. Chemical synthesis methods may include, for example, the phosphotriester method described by Narang, S. A., et al., Methods in Enzymology 68 (1979) 90-98, the phosphodiester method disclosed by Brown, E. L., et al., Methods in Enzymology 68 (1979) 109-151, the phosphoramidite method disclosed in Beaucage et al., Tetrahedron Letters 22 (1981) 1859, the H-phosphonate method disclosed in Garegg, et al., Chem. Scr. 25 (1985) 280-282, and the solid support method disclosed in U.S. Pat. No. 4,458,066. Particularly preferred is the phosphoramidite method. Therefore, in another embodiment of the invention, a method for the chemical synthesis of an oligomeric compound according to the invention is provided, comprising the steps of
(a) providing a compound according to the invention, wherein $R^2$ is phosphoramidite and $R^3$ is a protecting group,
(b) providing a 5'-OH group of a nucleoside or a modified nucleoside bound to a solid phase by the 3'-OH group, or providing a 5'-OH group of an oligonucleotide or a modified oligonucleotide bound to a solid phase by the 3'-OH group of the nucleotide or modified nucleotide at the 3'end of the oligonucleotide or a modified oligonucleotide, (c) reacting the phosphorous atom of the phosphoramidite with the 5'-OH group to form a phosphite ester and oxidizing the phosphite ester to a phosphotriester, (d) optionally reacting any unreacted 5'-OH group of step (c) with another compound to prevent any further reactions of the unreacted 5'-OH group of step (c) in the following steps ("Capping"-reaction), (e) optionally repeating steps (a) to (d) with phosphoramidite derivatives of nucleosides or modified nucleosides after removal of the protecting group of the compound according to the invention, and (f) cleaving the oligomeric compound from the solid phase, removing the protecting groups and thereby converting the phosphotriester to a phosphodiester, and (g) isolating the oligomeric compound.

A preferred embodiment of the invention is related to a method to synthesize a compound according to the invention, comprising the steps of (a) providing a compound of the formula III,

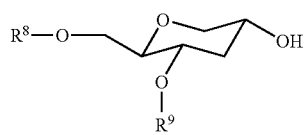

Formula III whereby $R^8$ and $R^9$ either represent a first and a second O-protecting group or form together a benzylidene residue, whereby the methylene group thereof is linked to the two oxygen atoms of formula III, (b) reacting said compound of formula III with a leaving group like p-toluenesulfonylchloride to obtain the derivative of formula IV,

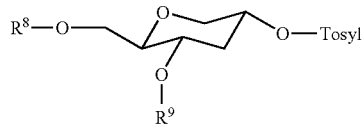

Formula IV whereby -Tosyl represents the p-toluenesulfonyl residue;

(c) reacting the compound of formula IV with azide to obtain the compound of formula V;

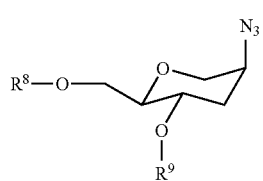

Formula V (d) deprotecting the 4- and 6-oxygen atoms in the compound of formula V to obtain the compound of formula VI;

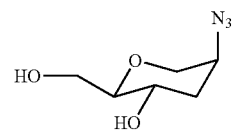

Formula VI (e) protecting the 6-OH moiety with a 4,4'-dimethoxytrityl-residue to obtain the compound of formula VII,

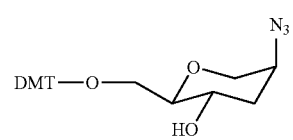

Formula VII whereby DMT-represents the 4,4'-dimethoxytrityl-residue;

(f) reducing the azido-function with a reducing agent like triphenylphosphane to obtain the compound of formula VIII;

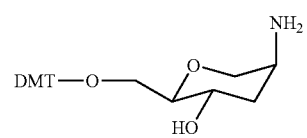

Formula VIII (g) coupling a residue $R^1$ or, optionally, a residue $R^1$ with a linking moiety X to the 2 amino function to obtain the compound of formula IX, wherein n is 0 or 1,

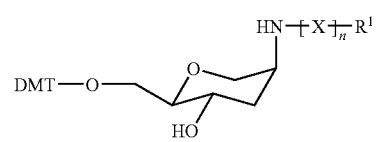

Formula IX (h) introducing a phosphoramidite function to the 4-oxygen to obtain the compound of formula X, wherein n is 0 or 1,

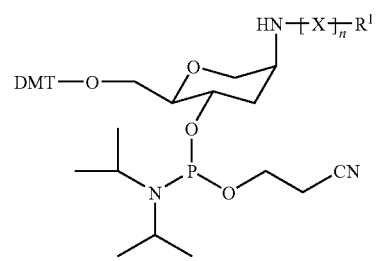

Formula X (i) and isolating the compound.

A preferred embodiment of the invention is related to a method to synthesize a compound according to the invention, comprising the steps of (a) providing a compound of the formula III,

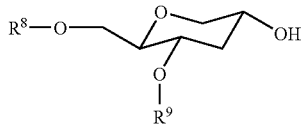

Formula III (b) whereby $R^8$ and $R^9$ either represent a first and a second O-protecting group or form together a benzylidene residue; whereby the methylene group thereof is linked to the two oxygen atoms of formula III;

(c) reacting said compound of formula III with a leaving group like p-toluenesulfonylchloride to obtain the derivative of formula IV,

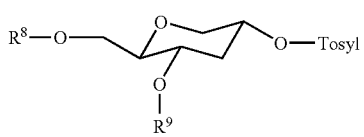

Formula IV whereby —Tosyl represents the p-toluenesulfonyl residue;

(d) reacting the compound of the formula IV with another leaving group like bromide to obtain the compound of formula XI;

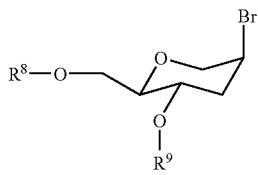

Formula XI (e) reacting the compound of formula XI with azide to obtain the compound of formula XII;

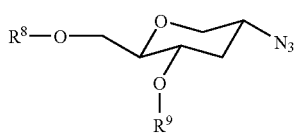

Formula XII (f) deprotecting the 4- and 6-oxygen atoms in the compound of formula XII to obtain the compound of formula XIII;

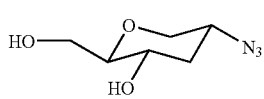

Formula XIII (g) protecting the 6-OH moiety with a 4,4'-dimethoxytrityl-residue to obtain the compound of formula XIV,

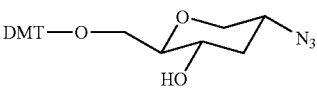

Formula XIV whereby DMT—represents the 4,4'-dimethoxytrityl-residue;

(h) reducing the azido-function with a reducing agent like triphenylphosphane to obtain the compound of formula XV;

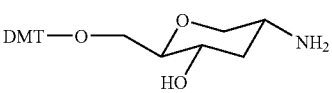

Formula XV (i) coupling a residue $R^1$ or, optionally, a residue $R^1$ with a linking moiety X to the 2 amino function to obtain the compound of formula XVI, wherein n is 0 or 1,

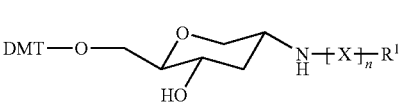

Formula XVI (j) introducing a phosphoramidite function to the 4'-oxygen to obtain the compound of formula XVII, wherein n is 0 or 1,

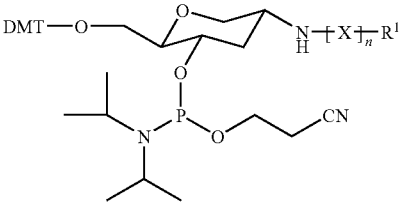

Formula XVII (k) and isolating the compound.

In another embodiment of the invention, the transfer of a compound according to the invention to a polynucleotide or an oligonucleotide applying terminal transferase is contemplated. The principal method is known to an expert skilled in the art. Therefore, in an embodiment of the invention a method for the enzymatic synthesis of a polymeric or an oligomeric compound according to the invention is provided comprising the steps of (a) incubating a compound according to the invention, wherein $R^3$ of said compound is a triphosphate, (b) with a 3'-OH group of the nucleotide or modified nucleotide at the 3'-end of an polynucleotide, oligonucleotide or a modified oligonucleotide in the presence of terminal transferase, whereby the compound is attached to the 3'-OH group, whereby pyrophosphate is released, and (c) isolating the polymeric or oligomeric compound.

In another embodiment, post-labelling of the oligomeric compounds according to the invention is contemplated. Therefore, in an embodiment of the invention a method to attach a label to an oligomeric compound according to the invention is provided, whereby $R^7$ of the oligomeric compound is a protecting group, comprising the steps of removing the protecting group $R^7$, and reacting the deprotected moiety of the oligomeric compound with the label.

The deprotected moiety is $NH_2$, OH or SH moiety, but preferably the $NH_2$ moiety.

Methods for performing these reaction steps are known to the expert skilled in the art.

In another embodiment of the invention a method for the detection of a target nucleic acid in a sample is provided comprising the steps of (a) providing a sample suspected to contain the target nucleic acid (b) providing an oligomeric compound according to the invention, which is essentially complementary to a part or all of the target nucleic acid, (c) optionally amplifying the target nucleic acid with a template-dependent DNA polymerase and primers (c) contacting the sample with the oligomeric compound under conditions for binding the oligomeric compound to the target nucleic acid, (d) determining the binding product or the degree of hybridization between the target nucleic acid and the oligomeric compound as a measure of the presence, absence or amount of the target nucleic acid.

Preferably oligomeric compound according to the invention comprises two labels, preferably two fluorescent labels.

The amplification is performed preferably with the polymerase chain reaction which specifically amplifies target nucleic acids to detectable amounts. Other possible amplification reactions are the Ligase Chain Reaction (LCR; Wu, D. Y., and Wallace, R. B., Genomics 4 (1989) 560-569; and Barany, F., Proc. Natl. Acad. Sci. USA 88 (1991)189-193); Polymerase Ligase Chain Reaction (Barany, F., PCR Methods and Applic. 1 (1991) 5-16); Gap-LCR (WO 90/01069); Repair Chain Reaction (EP 0439182 A2), 3SR (Kwoh, D. Y., et al., Proc. Natl. Acad. Sci. USA 86 (1989) 1173-1177; Guatelli, J. C., et al., Proc. Natl. Acad. Sci. USA 87 (1990) 1874-1878; WO 92/08808), and NASBA (U.S. Pat. No. 5,130,238). Further, there are strand displacement amplification (SDA), transcription mediated amplification (TMA), and Qβ-amplification (for a review see e.g. Whelen, A. C., and Persing, D. H., Annu. Rev. Microbiol. 50 (1996) 349-373; Abramson, R. D., and Myers, T. W., Current Opinion in Biotechnology 4 (1993) 41-47).

The preferred template-dependent DNA polymerase is Taq polymerase. In a preferred embodiment of the method, the format used in the TaqMan® assay is contemplated whereby the oligomeric compound according to the invention is used as a probe. Therefor, the oligomeric compound according to the invention comprises a label as $R^7$ which is preferably a fluorescent label, preferably fluorescein. The oligomeric compound according to the invention may further comprise other fluorescent labels wherein the emission wavelengths of one of the fluorescent labels overlaps the absorption wavelengths of another of the fluorescent labels. Preferably, the oligomeric compound further comprises a second fluorescent label acting as a quenching agent, that quenches the fluorescence emission of the fluorescent label, which can be fluorescein. Preferably the quenching agent is a fluorescent rhodamine or cyanine. The quenching agent can also be a non-fluorescent compound or dye as dabcyl ("Dark quencher"). The oligomeric compound according to the invention cannot be extended enzymatically to be used as probe in the TaqMan® format as principally set out in U.S. Pat. No. 5,210,015, U.S. Pat. No. 5,478,972, or U.S. Pat. No. 5,804,375. Preferably, the monomeric unit at the 3'-end of the oligomeric compound is a 2',3'-dideoxynucleotide or a 3'-phosphorylated nucleotide. Preferably for use in the TaqMan® format, the compound according to the invention with a label as well as a second compound with the label may be located internally in the modified oligonucleotide according to the invention or at the 5'-end and/or 3'-end of the modified oligonucleotide according to the invention. In consequence for the format used in the TaqMan® assay, in the determination step of the method, the spatial relationship between the fluorescent label and the second label, i.e. the quenching agent, subsequent to hybridization is altered, preferably by exonuclease hydrolysis of a template-dependent DNA polymerase, preferably the Taq-Polymerase, of the nucleic acid binding compound whereby release of label occurs as a result of exonuclease hydrolysis. The degree of hybridization between the oligomeric compound according to the invention and the nucleic acid is determined by the quantity of label that is released from the oligomeric compound according to the invention subsequent to hybridization. Therefore it is a preferred embodiment of the invention, that in step (d) the degree of hybridization is determined by the quantity of label that is released from the oligomeric compound hybridized to the nucleic acid by exonuclease hydrolysis by the template-dependent DNA polymerase.

In a very preferred embodiment of the invention related in more detail to the TaqMan® assay format, a method for the detection of a target nucleic acid in a sample is provided comprising the steps of (a) contacting a sample comprising single-stranded nucleic acids with an oligonucleotide containing a sequence complementary to a region of the target nucleic acid and an oligomeric compound according to the invention, whereby $R^7$ is a fluorescent label and the oligomeric compound contains a second fluorescent label, and whereby said oligomeric compound contains a sequence complementary to a second region of the same target nucleic acid sequence strand, but not including the nucleic acid sequence defined by the oligonucleotide, to create a mixture of duplexes during hybridization conditions, wherein the duplexes comprise the target nucleic acid annealed to the oligonucleotide and to the oligomeric compound such that the 3' end of the first oligonucleotide is upstream of the 5' end of the oligomeric compound, (b) maintaining the mixture of step (a) having a 5' to 3' nuclease activity under conditions sufficient to permit the 5' to 3' nuclease activity of the polymerase to cleave the annealed, oligomeric compound and release labelled fragments; and (c) detecting and/or measuring the release of labelled fragments.

In another embodiment of the invention, a format for the use in the LightCycler® instrument is provided as described in U.S. Pat. No. 6,174,670. For use in the formats used in the LightCycler® Instrument, the compound according to invention will be preferably at the 3'- or 5'-end, i.e. the monomeric unit at the 3'- or 5'-end of the oligomeric compound after the synthesis thereof. These formats apply the fluorescent resonance energy transfer technology (see, for example, U.S. Pat. Nos. 4,996,143, 5,565,322, 5,849,489, and 6,162,603) and are based on the fact that when a donor and a corresponding acceptor fluorescent label are positioned within a certain distance of each other, energy transfer takes place between the two fluorescent labels that can be visualized or otherwise detected and/or quantitated. As used herein, two probes, each containing a fluorescent label, whereby at least one thereof is an oligomeric compound according to the invention, can hybridize to an amplification product at particular positions determined by the complementarity of the probes to the target nucleic acid. The fluorescent label according to the invention of the oligomeric compound according to the invention may be a donor or acceptor fluorescent label. Upon hybridization of the probes to the amplification product at the appropriate positions, a FRET signal is generated. Fluorescent analysis can be carried out using, for example, a photon counting epifluorescent microscope system (containing the appropriate dichroic mirror and filters for monitoring fluorescent emission at the particular range), a photon counting photomultiplier system, or a fluorometer. Excitation to initiate energy transfer can be carried out with an argon ion laser, a high intensity mercury (Hg) arc lamp, a fiber optic light source, or other high intensity light source appropriately filtered for excitation in the desired range. As used herein with respect to donor and corresponding acceptor fluorescent labels, "corresponding" refers to an acceptor fluorescent label having an excitation spectrum that overlaps the emission spectrum of the donor fluorescent label. Accordingly, efficient non-radiative energy transfer can be produced there between. The preferred fluorescent label is fluorescein as the donor fluorescent label, whereby the acceptor fluorescent label is rhodamine, however, preferred is a cyanine dye, preferably Cy5 as described in U.S. Pat. No. 6,174,670.

Therefore, in an embodiment of the invention, a method for detecting the presence or absence of a target nucleic acid in a sample is provided, comprising the steps of:

performing at least one cycling step, wherein a cycling step comprises an amplifying step and a hybridizing step, wherein said amplifying step comprises contacting said sample with primers to produce an amplification product if target nucleic acid is present in said sample, wherein said hybridizing step comprises contacting said sample with a pair of probes, wherein the members of said pair of probes hybridize to said amplification product within no more than five nucleotides of each other, wherein a first probe of said pair of probes is labeled with a donor fluorescent label and wherein a second probe of said pair of probes is labeled with a corresponding acceptor fluorescent label;

and detecting the presence or absence of fluorescence resonance energy transfer between said donor fluorescent label of said first probe and said acceptor fluorescent label of said second probe, wherein the presence of FRET is indicative of the presence of the target nucleic acid in the sample, and wherein the absence of FRET is indicative of the absence of the target nucleic acid in the sample.

Therefore, in a preferred embodiment of the invention, a method for detecting a target nucleic acid in a sample is provided, comprising the steps of amplifying the nucleic acid by polymerase chain reaction in the presence of two nucleic acid probes, whereby a probe is an oligomeric compound according to the invention, that hybridize to adjacent regions of the target nucleic acid, one of said probes being labeled with an acceptor fluorescent label and the other probe labeled with a donor fluorescent label of a fluorescence energy transfer pair such that upon hybridization of the two probes with the target nucleic acid, the donor and acceptor fluorescent labels are within 25 nucleotides of one another, said polymerase chain reaction comprising the steps of adding a thermostable polymerase, nucleotides and primers for the target nucleic acid to the sample and thermally cycling the sample between at least a denaturation temperature and an elongation temperature; exciting the biological sample with light at a wavelength absorbed by the donor fluorescent label and detecting fluorescent emission from the fluorescence energy transfer pair.

In another preferred embodiment of the invention, a method for the detection of a target nucleic acid in sample is provided comprising the steps of amplifying the nucleic acid by polymerase chain reaction in the presence of two nucleic acid probes, whereby a probe is an oligomeric compound according to the invention, that hybridize to adjacent regions of the nucleic acid, one of said probes being labeled with an acceptor fluorescent label and the other probe labeled with donor fluorescent label of a fluorescence energy transfer pair such that upon hybridization of the two probes with the target nucleic acid, the donor and acceptor fluorescent labels are within 25 nucleotides of one another, said polymerase chain reaction comprising the steps of adding a thermostable polymerase, nucleotides and primers for the target nucleic acid to the sample and thermally cycling the sample between at least a denaturation temperature and an elongation temperature; exciting the sample with light at a wavelength absorbed by the donor label and monitoring temperature dependent fluorescence from the fluorescence energy transfer pair.

In another preferred embodiment a kit of parts is contemplated by the invention whereby the kit contains a template-dependent polymerase having 3' to 5' exonucleolytic activity, preferably the Taq Polymerase, a set of primers, nucleotides and a oligomeric compound according to the invention. Such kits known in the art further comprise plastics ware which can be used during the amplification procedure as e.g. microtitre plates in the 96 or 384 well format or just ordinary reaction tubes manufactured e.g. by Eppendorf, Hamburg, Germany and all other reagents for carrying out the method according to the invention.

In another embodiment of the invention, the kit contains further reagents for isolating the nucleic acid. Therefore, the kit can additionally contain a material with an affinity to nucleic acids, preferably the material with an affinity to nucleic acids comprises a material with a silica surface. Preferably, the material with a silica surface is a glass. Most preferably, the material with an affinity to nucleic acids is a composition comprising magnetic glass particles as described in WO 96/41811 or WO 01/37291. The kit can further or additionally comprise a lysis buffer containing e.g. chaotropic agents, detergents or alcohols or mixtures thereof which allows the lysis of cells and separately a protease, e.g. proteinase K, for the digestions of unwanted proteins. These components of the kit according to the invention may be provided separately in tubes or storage containers. Depending on the nature of the components, these may be even provided in a single tube or storage container. The kit may further or additionally comprise a washing solution which is suitable for the washing step of the magnetic glass particles when DNA or RNA is bound thereto. This washing solution may contain ethanol and/or chaotropic agents in a buffered solution or solutions with an acidic pH without ethanol and/or chaotropic agents as described above. Often the washing solution or other solutions are provided as stock solutions which have to be diluted before use. The kit may further or additionally comprise an eluent or elution buffer, i.e. a solution or a buffer (e.g. 10 mM Tris, 1 mM EDTA, pH 8.0) or pure water to elute the DNA or RNA bound to the magnetic glass particles. Further, additional reagents or buffered solutions may be present which can be used for the purification process of a nucleic acid, i.e. DNA or RNA.

The following examples, references, sequence listing and figures are provided to aid the understanding of the present invention, the true scope of which is set forth in the appended claims. It is understood that modifications can be made in the procedures set forth without departing from the spirit of the invention

EXAMPLES

Example 1

1.1 Preparative Examples—General Description of Synthesis

The synthesis of the novel building blocks 8 and 15 starts with commercially available 4,6-O-benzylidene-1,5-anhydro-3-deoxy-D-glucitol 1 and is outlined in FIG. 1. First, the 2-hydroxy group was tosylated in 89% yield to give 2 which served as intermediate for the final mannitol isomeric reagent. To obtain the corresponding glucitol derivative the configuration at C-2 had to be inverted. This was achieved by $S_N2$ type nucleophilic substitution reaction with lithium bromide in pyridine to give 9 in 66% yield. Intermediates 2 and 9 were reacted with sodium azide in DMF to again invert the configuration at C-2 by $S_N2$ type nucleophilc substitution reaction to yield the mannitol isomeric 2-azido derivative 3 and the glucitol isomeric 2-azido derivative 10 in 97% and 66% yield, respectively. Deprotection of the benzylidene group with 80% acetic acid proceeded almost quantitatively to give 4 (93%) and 11 (98%). Thereafter, dimethoxytrityl group was introduced in 77% yield to give intermediates 5 and 12. Reduction of the azido group by Staudinger reaction yielded 2-amino derivatives 6 and 13 in 93% and 91% yield, respectively. Reaction of 6 and 13 with 6-carboxyfluorescein dipivaloate which was in-situ activated with isobutyl chloroformate in DMF and N-methylmorpholine gave compounds 7 and 14 in 75% yield. Reaction with 2-cyanoethoxy-diisopropylamino-chloro-phosphane and Hünigs base in dichloromethane led to the corresponding fluorescein labeled phosphoramidites in the mannitol configuration (8) in 81% yield and in the glucitol configuration (15) in 88% yield, respectively.

Starting from 4,6-O-benzylidene-1,5-anhydro-3-deoxy-D-glucitol 1 an overall-yield of 34.9% for the dipivaloyl protected 6-carboxyfluorescein labeled posphoramidite 8 in the mannitol configuration and 17.6% for the corresponding phosphoramidite 15 in the glucitol configuration could be achieved which is higher than the overall yield of the Biogenex linker synthesis route (U.S. Pat. No. 6,130,323).

FAM labelled phosphoramidites 8 and 15 were characterized by $^1$H-NMR, $^{31}$P-NMR and HPLC. Besides superior synthetic accessibility regarding ease of synthesis steps and yields there are additional advantages of the new monomers compared to the Biogenex derivatives. Both orientations of the label molecule within an oligonucleotide showing either to the 5'-direction or to the 3'-direction can be readily achieved by using either the building blocks in the mannitol configuration (8) or in the glucitol configuration (15). This brings advantages in some FRET applications. In case of use of lipophilic labels additional ether function in the hexitol ring is advantageous with respect to solubility.

1.2 Preparative Examples—Detailed Description of Synthesis

1.2.1 1,5-Anhydro-2-O-tosyl-4,6-O-benzylidene-3-deoxy-D-glucitol (2)

15 g (63.8 mmole) of 1,5-anhydro-4,6-O-benzylidene-3-deoxy-D-glucitol (CMS Chemicals Ltd.) and 16.6 g (86.2 mmole) of p-toluenesulfonylchloride were dissolved in 80 ml of pyridine and stirred overnight at r.t. Thereafter, 300 ml of water were added whereby the product crystallizes. The reaction mixture was stirred for 5 h at +4° C. for completion of crystallization. Solid was filtered off, washed with cold water and dried at high vacuum over blue-indication silica gel to give 22.0 g (88%) of a colorless solid.

$^1$H-NMR (DMSO-d$_6$, in ppm): 7.86 (d, 2H, Tos), 7.51 (d, 2H, Tos), 7.41-7.34 (m, 5H, benzylidene), 5.56 (s, 1H, benzylidene-CH), 4.56 (m, 1H, glucitol-C-2), 4.18/4.14 (dd, 1H, glucitol-CH), 3.84/3.80 (dd, 1H, glucitol-CH), 3.62-3.53 (m, 2H, glucitol-CH), 3.43-3.37 (m, 1H, glucitol-CH), 3.31-3.25 (m, 1H, glucitol-CH), 2.43 (s, 3H, CH$_3$),2.14 (m, 1H, glucitol-C-3-H), 1.75 (q, 1H, glucitol-C-3-H)

1.2.2 1,5-Anhydro-2-azido-4,6-O-benzylidene-2,3-dideoxy-D-mannitol (3)

10 g (25.0 mmole) of 1,5-anhydro-2-O-tosyl-4,6-O-benzylidene-3-deoxy-D-glucitol (2) and 6.5 g (100 mmole) of sodium azide were dissolved in 250 ml of DMF and stirred at 130° C. for 4.5 h. Thereafter, DMF was evaporated. The residue was dissolved in 400 ml of ethyl acetate and washed twice with 200 ml of 0.1 M phosphate buffer pH 7.5. The organic layer was separated, dried over Na$_2$SO$_4$., filtered and evaporated. The residue was dissolved in 25 ml of ethyl acetate and purified by flash-chromatography over silica gel. (n-hexane/ethyl acetate 2:3). Product fractions were combined, evaporated and dried at high vacuum to give 6.5 g (97%) of a colorless solid.

$^1$H-NMR (DMSO-d$_6$, in ppm): 7.43-7.35 (m, 5H, benzylidene), 5.65 (s, 1H, benzylidene-CH), 4.17-4.12 (m, 2H, mannitol-CH), 3.90-3.80 (m, 2H, mannitol-CH), 3.72-3.65 (m, 2H, mannitol-CH), 3.39-3.32 (m, 1H, mannitol-C-2-H), 2.12-2.07 (m, 1H, mannitol-C-3-H), 1.93 1.84 (m, 1H, mannitol-C-3-H)

1.2.3 1,5-Anhydro-2-azido-2,3-dideoxy-D-mannitol (4)

13 g (49.9 mmole) of 1,5-anhydro-2-azido-4,6-O-benzylidene-2,3-dideoxy-D-mannitol (3) were dissolved in 700 ml of 80% acetic acid and stirred for 1 h at 80° C. Thereafter, the reaction mixture was cooled to r.t. and evaporated to dryness. The residue was dissolved in 50 ml of ethyl acetate, then 250 ml of n-hexane were added. The reaction flask was stored overnight at 4° C. Supernatant was decanted and oily residue was dried at high vacuum to give 8.0 g (93%) of a yellow oil.

$^1$H-NMR (DMSO-d$_6$, in ppm): 4.98 (sb, 1H, OH), 4.58 (sb, 1H, OH), 3.81-3.77 (m, 1H, mannitol-CH), 3.70-3.65 (m, 1H, mannitol-CH), 3.57-3.37 (m, 3H, mannitol-CH), 3.04-2.99 (m, 1H, mannitol-C-2-H), 2.09-2.02 (m, 1H, mannitol-C-3-H), 1.66-1.58 (m, 1H, mannitol-C-3-H)

1.2.4 6-O-(4,4'-Dimethoxytrityl)-1,5-anhydro-2-azido-2,3-dideoxy-D-mannitol (5)

7.6 g (44 mmole) of 1,5-anhydro-2-azido-2,3-dideoxy-D-mannitol (4) were coevaporated with 3×40 ml of pyridine and then dissolved in 120 ml of pyridine. Thereafter, 19.6 g (53.3 mmole) of 4,4'-dimethoxytritylchloride in 120 ml of pyridine are added at r.t. within 1 h under stirring. The reaction mixture was stirred for another 2 h at r.t. Then pyridine was evaporated and the residue was dissolved in 800 ml of ethyl acetate und washed twice with 400 ml of 5% sodium hydrogencarbonate solution. Organic layer was separated, dried over sodium sulfate, filtered and evaporated to dryness. The residue was dissolved in 30 ml of ethyl acetate and purified by flash-chromatography over silica gel (n-hexane/ethyl acetate/1% triethylamine gradient). Product fractions were combined, evaporated and dried at high vacuum to yield 15.8 g (77%) of a yellowish foam.

$^1$H-NMR (DMSO-d$_6$, in ppm): 7.41 (d, 2H, DMT), 7.32-7.18 (m, 7H, DMT), 6.87 (d, 4H, DMT), 4.86 (d, 1H, OH), 3.89 (m, 2H, mannitol-C-1-H), 3.73 (s, 6H, OCH$_3$), 3.60-3.55

(m, 1H, mannitol-CH), 3.48-3.43 (m, 1H, mannitol-CH), 3.34-2.27 (m, 2H, mannitol-C-6-H), 2.99 (m, 1H, mannitol-C-H-2), 2.09-2.04 (m, 1H, mannitol-C-3-H), 1.68-1.59 (m, 1H, mannitol-C-3-H)

1.2.5 6-O-(4,4'-Dimethoxytrityl)-1,5-anhydro-2-amino-2,3-dideoxy-D-mannitol (6)

6.5 g (13.7 mmole) of 6-O-DMT-1,5-anhydro-2-azido-2,3-dideoxy-D-mannitol (5) were dissolved in 70 ml of pyridine and 50 ml of 32% aqueous ammonia, then 6.1 g (23.3 mmole) of triphenylphosphane are added. The reaction mixture was stirred for 18 h at r.t. Thereafter the reaction mixture was evaporated. The residue was dissolved in 400 ml of ethyl acetate und washed twice with 200 ml of 5% sodium hydrogencarbonate solution. Organic layer was separated, dried over sodium sulfate, filtered and evaporated to dryness. The residue was dissolved in 10 ml of ethyl acetate and purified by flash-chromatography over silica gel (ethyl acetate/methanol/1% triethylamine gradient). Product fractions were combined, evaporated and dried at high vacuum to yield 5.7 g (93%) of a colorless foam.

$^1$H-NMR (CDCl$_3$, in ppm): 7.42 (d, 2H, DMT), 7.34-7.19 (m, 7H, DMT), 6.84 (d, 4H, DMT), 3.89-3.80 (m, 1H, mannitol-CH), 3.79 (s, 6H, OCH$_3$), 3.69-3.65 (m, 1H, mannitol-CH), 3.52-3.46 (2m, 2H, mannitol-CH), 3.32-3.26 (m, 2H, mannitol-C-H-1), 3.13 (m, 1H, mannitol-C-H-2), 2.10-1.90 (m, 4H, mannitol-C-3-H, NH$_2$, OH), 1.68-1.59 (m, 1H, mannitol-C-3-H)

1.2.6 6-O-(4,4'-Dimethoxytrityl)-2-(O,O'-dipivalyol-fluoresceinyl-6-carboxamido)-1,5-anhydro-2,3-dideoxy-D-mannitol (7)

0.76 g (1.27 mmole) of 6-carboxyfluorescein-dipivaloate and 155 µl (1.4 mmole) of N-methylmorpholine were dissolved in 15 ml of DMF under Ar-atmosphere. Thereafter, reaction mixture was cooled to −25° C. and 170 µl (1.3 mmole) of i-butyl chloroformate were added. After stirring the reaction mixture for 30 min at −25° C. 0.56 g (1.27 mmole) of 6-O-DMT-1,5-anhydro-2-amino-2,3-dideoxy-D-mannitol (6) and 140 µl (1.3 mmole) of N-methylmorpholine in 10 ml of DMF were added within 15 min. Thereafter the reaction mixture was stirred for 1 h at −25° C. Then DMF was evaporated. The residue was dissolved in 200 ml of ethyl acetate und washed twice with 100 ml of 0.1 M sodium phosphate buffer pH 7.5. Organic layer was separated, dried over sodium sulfate, filtered and evaporated to dryness. The residue was dissolved in 5 ml of ethyl acetate and purified by flash-chromatography over silica gel (n-hexane/ethyl acetate/1% triethylamine gradient). Product fractions were combined, evaporated and dried at high vacuum to yield 0.92 g (75%) of a colorless solid.

$^1$H-NMR (CDCl$_3$, in ppm): 8.09 (d, 1H, fluorescein), 7.93 (d, 1H, fluorescein), 7.56 (s, 2H, fluorescein), 7.41 (d, 2H, DMT), 7.33-7.25 (m, 7H, DMT), 7.09 (s, 2H, fluorescein), 6.85-6.79 (m, 8H, 4H from DMT, 4H from fluorescein), 6.55 (d, 1H, NH), 4.35 (m, 1H, mannitol-CH), 3.91-3.70 (2m, 2H, mannitol-CH), 3.81 (s, 6H, OCH$_3$), 3.64-3.60 (m, 1H, mannitol-CH), 3.52-3.46 (m, 1H, mannitol-CH), 3.36-3.30 (m, 2H, mannitol-CH), 2.88 (m, 1H, mannitol-CH), 2.39 (m, 1H, mannitol-C-3-H), 1.70-1.60 (m, 2H, mannitol-C-3-H, OH), 1.37 (s, 18H, t-butyl)

1.2.7 6-O-(4,4'-Dimethoxytrityl)-2-(O,O'-dipivalyol-fluoresceinyl-6-carboxamido)-1,5-anhydro-2,3-dideoxy-D-mannitol-4-O-[N,N-diisopropyl-(2-cyanoethyl)]-phosphoramidit (8)

0.92 g (0.94 mmole) of 6-O-(4,4'-Dimethoxytrityl)-2-(O,O'-dipivalyol-fluoresceinyl-6-carboxamido)-1,5-anhydro-2,3-dideoxy-D-mannitol (7) were dissolved in 30 ml of dichloromethane under Ar-atmosphere. Thereafter 285 µl (1.67 mmole) of N-ethyldiisopropylamine, and within 15 min 296 mg (1.26 mmole) of chloro-2-cyanoethyoxy-diisopropylamino-phosphane in 15 ml of dichloromethane were added. The reaction mixture was stirred for 1 h at r.t. Then 150 ml of dichloromethane were added. Reaction mixture was washed twice with 100 ml of 0.1 M sodium phosphate buffer pH 7.5. Organic layer was separated, dried over sodium sulfate, filtered and evaporated to dryness. The residue was dissolved in 5 ml of n-hexane/acetone 1:1 and purified by flash-chromatography over silica gel (n-hexane/acetone gradient). Product fractions were combined, evaporated and dried at high vacuum to yield 0.9 g (81%) of a colorless foam.

$^1$H-NMR (CDCl$_3$, in ppm): 8.02-6.76 (m, 23H, 13H from DMT, 9H from fluorescein, NH), 4.35-3.12 (m, 11H, CH$_2$OP, 7H from mannitol, CH (iPr)), 3.80/3.79 (2s, 6H, OCH$_3$), 2.47 (t, 2H, CH$_2$CN), 2.35-2.13 (m, 1H, mannitol-C-H-3), 1.85-1.72 (m, 1H, mannitol-C-3-H), 1.37/1.32 (3s, 18H, t-butyl), 1.07-0.84 (3d, 12H, CH$_3$ from iPr) $^{31}$P-NMR (CDCl$_3$, in ppm): 150.1/148,2

1.2.8 1,5-Anhydro-2-bromo-4,6-O-benzylidene-2,3-dideoxy-D-mannitol (9)

3.0 g (7.8 mmole) of 1,5-anhydro-2-O-tosyl-4,6-O-benzylidene-3-deoxy-D-glucitol (2) and 2.2 g (25 mmole) of lithium bromide were dissolved in 60 ml of pyridine and stirred at 60° C. for 7 days. Thereafter, pyridine was evaporated. The residue was dissolved in 5 ml of ethyl acetate and purified by flash-chromatography over silica gel.(n-hexane/ethyl acetate gradient). Product fractions were combined, evaporated and dried at high vacuum to give 1.5 g (64%) of a colorless solid.

$^1$H-NMR (DMSO-d$_6$, in ppm): 7.44-7.34 (m, 5H, benzylidene), 5.72 (s, 1H, benzylidene-CH), 4.80 (m, 1H, mannitol-CH), 4.17 (m, 1H, mannitol-CH), 4.08 (m, 1H, mannitol-CH), 3.94 (m, 2H, mannitol-CH), 3.75 (t, 1H, mannitol-CH), 3.46-3.39 (m, 1H, mannitol-CH), 2.29-2.18 (m, 2H, mannitol-C-3-H)

1.2.9 1,5-Anhydro-2-azido-4,6-O-benzylidene-2,3-dideoxy-D-glucitol (10)

1.45 g (4.85 mmole) of 1,5-anhydro-2-bromo-4,6-O-benzylidene-3-deoxy-D-mannitol (9) and 1.26 g (19.4 mmole) of sodium azide were dissolved in 30 ml of DMF and stirred at 90° C. for 7 h. Thereafter, the reaction mixture was evaporated and purified by flash-chromatography over silica gel.(n-hexane/ethyl acetate 6:1). Product fractions were combined, evaporated and dried at high vacuum to give 0.83 g (66%) of a colorless solid.

$^1$H-NMR (DMSO-d$_6$, in ppm): 7.44-7.36 (m, 5H, benzylidene), 5.62 (s, 1H, benzylidene-CH), 4.20-4.15 (m, 1H, glucitol-CH), 4.00-3.96 (m, 1H, glucitol-CH), 3.86-3.59 (2m, 3H, glucitol-CH), 3.32-3.21 (m, 2H, glucitol-CH), 2.42-2.38 (m, 1H, glucitol-C-3-H), 1.59 (q, 1H, glucitol-C-3-H)

1.2.10 1,5-Anhydro-2-azido-2,3-dideoxy-D-glucitol (11)

0.8 g (3.1 mmole) of 1,5-anhydro-2-azido-4,6-O-benzylidene-2,3-dideoxy-D-glucitol (10) were dissolved in 80 ml of 80% acetic acid and stirred for 1 h at 80° C. Thereafter, the reaction mixture was cooled to r.t. and evaporated to dryness. The residue was dissolved in 4 ml of ethyl acetate, then 40 ml of n-hexane were added. Supernatant was decanted and oily residue was dried at high vacuum to give 0.52 g (98%) of a colorless oil.

$^1$H-NMR (DMSO-d$_6$, in ppm): 5.02 (db, 1H, OH), 4.52 (tb, 1H, OH), 3.90-3.85 (m, 1H, glucitol-CH), 3.67-3.58 (m, 2H, glucitol-CH), 3.40-3.31 (m, 2H, glucitol-CH), 3.05-2.92 (2m, 2H, glucitol-CH), 2.28 (m, 1H, glucitol-C-3-H), 1.32 (q, 1H, mannitol-C-3-H)

1.2.11 6-O-(4,4'-Dimethoxytrityl)-1,5-anhydro-2-azido-2,3-dideoxy-D-glucitol (12)

0.52 g (3.0 mmole) of 1,5-anhydro-2-azido-2,3-dideoxy-D-glucitol (11) were dissolved in 9 ml of pyridine. Thereafter, 1.1 g (3.2 mmole) of 4,4'-dimethoxytritylchloride in 9 ml of pyridine are added at r.t. within 30 min under stirring. The reaction mixture was stirred for another 3 h at r.t. Then pyridine was evaporated and the residue was dissolved in 100 ml of ethyl acetate und washed twice with 60 ml of 5% sodium hydrogencarbonate solution. Organic layer was separated, dried over sodium sulfate, filtered and evaporated to dryness. The residue was dissolved in 5 ml of ethyl acetate and purified by flash-chromatography over silica gel (n-hexane/ethyl acetate/1% triethylamine gradient). Product fractions were combined, evaporated and dried at high vacuum to yield 1.1 g (77%) of a colorless foam.

$^1$H-NMR (DMSO-$d_6$, in ppm): 7.40 (d, 2H, DMT), 7.32-7.18 (m, 7H, DMT), 6.87 (d, 4H, DMT), 4.99 (d, 1H, OH), 3.99-2.98 (m, 7H, glucitol-CH), 3.73 (s, 6H, OCH$_3$), 2.30 (m, 1H, glucitol-C-3-H), 1.34 (m, 1H, glucitol-C-3-H)

1.2.12 6-O-(4,4'-Dimethoxytrityl)-1,5-anhydro-2-amino-2,3-dideoxy-D-glucitol (13)

1.1 g (2.3 mmole) of 6-O-DMT-1,5-anhydro-2-azido-2,3-dideoxy-D-glucitol (12) were dissolved in 11 ml of pyridine and 9 ml of 32% aqueous ammonia, then 1.0 g (3.9 mmole) of triphenylphosphane are added. The reaction mixture was stirred for 18 h at r.t. Thereafter the reaction mixture was evaporated. The residue was dissolved in 180 ml of ethyl acetate und washed twice with 100 ml of 5% sodium hydrogencarbonate solution. Organic layer was separated, dried over sodium sulfate, filtered and evaporated to dryness. The residue was dissolved in 5 ml of ethyl acetate and purified by flash-chromatography over silica gel (ethyl acetate/methanol/1% triethylamine gradient). Product fractions were combined, evaporated and dried at high vacuum to yield 0.94 g (91%) of a colorless foam.

$^1$H-NMR (DMSO-$d_6$, in ppm): 7.40 (d, 2H, DMT), 7.31-7.12 (m, 7H, DMT), 6.87 (d, 4H, DMT), 4.67 (sb, 1H, OH), 3.77 (m, 1H, glucitol-CH), 3.72 (s, 6H, OCH$_3$), 3.50-3.06 (m, 5H, 3H glucitol-CH, NH$_2$), 2.96 (dd, 1H, glucitol-CH), 2.82 (t, 1H, glucitol-CH), 2.63 (m, 1H, glucitol-CH), 2.06 (m, 1H, glucitol-C-3-H), 1.07 (q, 1H, glucitol-C-3-H)

1.2.13 6-O-(4,4'-Dimethoxytrityl)-2-(O,O'-dipivalyol-fluoresceinyl-6-carboxamido)-1,5-anhydro-2,3-dideoxy-D-glucitol (14)

1.22 g (2.0 mmole) of 6-carboxyfluorescein-dipivaloate and 255 µl (2.25 mmole) of N-methylmorpholine were dissolved in 25 ml of DMF under Ar-atmosphere. Thereafter, reaction mixture was cooled to −25° C. and 280 µl (2.1 mmole) of i-butyl chloroformate were added. After stirring the reaction mixture for 30 min at −25° C. 0.90 g (2.0 mmole) of 6-O-DMT-1,5-anhydro-2-amino-2,3-dideoxy-D-glucitol (13) and 225 µl (2.0 mmole) of N-methylmorpholine in 20 ml of DMF were added within 30 min. Thereafter the reaction mixture was stirred for 1 h at −25° C. Then DMF was evaporated. The residue was dissolved in 150 ml of ethyl acetate und washed twice with 100 ml of 0.1 M sodium phosphate buffer pH 7.5. Organic layer was separated, dried over sodium sulfate, filtered and evaporated to dryness. The residue was dissolved in 10 ml of ethyl acetate and purified by flash-chromatography over silica gel (n-hexane/ethyl acetate/1% triethylamine gradient). Product fractions were combined, evaporated and dried at high vacuum to yield 1.44 g (75%) of a colorless solid.

$^1$H-NMR (CDCl$_3$, in ppm): 8.09 (d, 2H, fluorescein), 7.42 (d, 2H, DMT), 7.33-7.22 (m, 8H, 7H from DMT, 1H from fluorescein), 7.06 (d, 2H, fluorescein), 6.85-6.77 (m, 8H, 4H from DMT, 4H from fluorescein), 6.33 (d, 1H, NH), 4.18 (m, 1H, glucitol-CH), 4.03-3.98 (m, 1H, glucitol-CH), 3.79 (s, 6H, OCH$_3$), 3.75 (m, 1H, glucitol-CH), 3.46 (m, 1H, glucitol-CH), 3.31-3.26 (m, 2H, glucitol-CH), 3.14-3.03 (m, 2H, glucitol-CH), 2.31 (m, 1H, mannitol-C-3-H), 1.62 (m, 1H, mannitol-C-3-H), 1.40 (b, 1H, OH), 1.38 (s, 18H, t-butyl)

1.2.14 6-O-(4,4'-Dimethoxytrityl)-2-(O,O'-dipivalyol-fluoresceinyl-6-carboxamido)-1,5-anhydro-2,3-dideoxy-D-glucitol-4-O-[N,N-diisopropyl-(2-cyanoethyl)]-phosphoramidit (15)

0.48 g (0.49 mmole) of 6-O-(4,4'-Dimethoxytrityl)-2-(O,O'-dipivalyol-fluoresceinyl-6-carboxamido)-1,5-anhydro-2,3-dideoxy-D-glucitol (14) were dissolved in 15 ml of dichloromethane under Ar-atmosphere. Thereafter 160 µl (0.89 mmole) of N-ethyldiisopropylamine, and within 15 min 170 mg (0.67 mmole) of chloro-2-cyanoethyoxy-diisopropylamino-phosphane in 7 ml of dichloromethane were added. The reaction mixture was stirred for 1 h at r.t. Then 100 ml of dichloromethane were added. Reaction mixture was washed twice with 50 ml of 0.1 M sodium phosphate buffer pH 7.5. Organic layer was separated, dried over sodium sulfate, filtered and evaporated to dryness. The residue was dissolved in 5 ml of n-hexane/acetone 1:1 and purified by flash-chromatography over silica gel (n-hexane/acetetone gradient). Product fractions were combined, evaporated and dried at high vacuum to yield 0.51 g (88%) of a colorless solid.

$^1$H-NMR (CDCl$_3$, in ppm): 8.12 (m, 2H, fluorescein), 7.52-7.21 (m, 10H, 9H from DMT, 1H from fluorescein), 7.08 (m, 2H, fluorescein), 6.86-6.78 (m, 8H, 4H from DMT, 4H from fluorescein), 6.51/6.39 (2d, 1H, NH), 4.30-3.17 (m, 11H, CH$_2$OP, 7H from glucitol, CH (iPr)), 3.80/3.79 (2s, 6H, OCH$_3$), 2.54/2.36 (t, 2H, CH$_2$CN), 2.45 (m, 1H, glucitol-C-H-3), 1.78-1.60 (m, 1H, glucitol-C-3-H), 1.38/1.37 (2s, 18H, t-butyl), 1.11-0.88 (4d, 12H, CH$_3$ from iPr)

$^{31}$P-NMR (CDCl$_3$, in ppm): 148.9/147.7

1.2.15 6-O-(4,4'-Dimethoxytrityl)-2-[N-(9-fluorenylmethoxycarbonyl)-6-aminohexanoylamido]-1,5-anhydro-2,3-dideoxy-D-mannitol (16)

0.87 g (2.8 mmole) of N-Fmoc-6-aminohexanoic acid and 300 µl (3.0 mmole) of N-methylmorpholine were dissolved in 25 ml of DMF under Ar-atmosphere. Thereafter, reaction mixture was cooled to −25° C. and 350 µl (2.8 mmole) of i-butyl chloroformate were added. After stirring the reaction mixture for 30 min at −25° C. 1.12 g (2.5 mmole) of 6-O-DMT-1,5-anhydro-2-amino-2,3-dideoxy-D-mannitol (6) and 270 µl (2.5 mmole) of N-methylmorpholine in 15 ml of DMF were added within 15 min. Thereafter the reaction mixture was stirred for 1 h at −25° C. Then DMF was evaporated. The residue was dissolved in 200 ml of ethyl acetate und washed twice with 100 ml of 0.1 M sodium phosphate buffer pH 7.5. Organic layer was separated, dried over sodium sulfate, filtered and evaporated to dryness. The residue was dissolved in 10 ml of n-hexane/ethyl acetate 1:4 and purified by flash-chromatography over silica gel (n-hexane/ethyl acetate gradient). Product fractions were combined, evaporated and dried at high vacuum to yield 1.35 g (70%) of a colorless foam.

$^1$H-NMR (CDCl$_3$, in ppm): 7.76 (d, 2H, Fmoc), 7.58 (d, 2H, Fmoc), 7.43-7.17 (m, 13H, 9H from DMT, 4H from Fmoc), 6.84 (d, 4H, DMT), 5.93 (d, 1H, NH), 4.89 (tb, 1H, NH), 4.37 (d, 2H, Fmoc), 4.20 (m, 2H, 1H from mannitol-CH, 1H from Fmoc), 3.79-3.67 (m, 1H, mannitol-CH), 3.77 (s, 6H, OCH$_3$), 3.56-3.01 (5m, 7H, 5H mannitol-CH, CH$_2$N), 2.25 (m, 1H, mannitol-C-3-H), 2.17 (t, 2H, CH$_2$CO), 1.65-1.33 (3m, 8H, mannitol-C-3-H, OH, CH$_2$ from hexanoyl)

1.2.16  6-O-(4,4'-Dimethoxytrityl)-2-[N-(9-fluorenyl-methoxycarbonyl)-6-aminohexanoylamido]-1,5-anhydro-2,3-dideoxy-D-mannitol-4-O-[N,N-diisopropyl-(2-cyanoethyl)]-phosphoramidit (17)

1.3 g (1.69 mmole) of 6-O-(4,4'-Dimethoxytrityl)-2-[N-(9-fluorenylmethoxycarbonyl)-6-aminohexanoylamido]-1,5-anhydro-2,3-dideoxy-D-mannitol (16) were dissolved in 45 ml of dichloromethane under Ar-atmosphere. Thereafter 550 µl (3.07 mmole) of N-ethyldiisopropylamine, and within 15 min 590 mg (2.31 mmole) of chloro-2-cyanoethyoxy-diisopropylamino-phosphane in 20 ml of dichloromethane were added. The reaction mixture was stirred for 1 h at r.t. Then 100 ml of dichloromethane were added. Reaction mixture was washed twice with 100 ml of 0.1 M sodium phosphate buffer pH 7.5. Organic layer was separated, dried over sodium sulfate, filtered and evaporated to dryness. The residue was dissolved in 10 ml of n-hexane/acetone 1:1 and purified by flash-hromatography over silica gel (n-hexane/acetone gradient). Product fractions were combined, evaporated and dried at high vacuum to yield 1.5 g (90%) of a colorless foam.

$^1$H-NMR (CDCl$_3$, in ppm): 7.77 (d, 2H, Fmoc), 7.61 (d, 2H, Fmoc), 7.50 (d, 2H, Fmoc), 7.43-7.19 (m, 1H, 9H from DMT, 2H from Fmoc), 6.82 (d, 4H, DMT), 6.31 (d, 1H, NH), 4.90 (t, 1H, NH), 4.38 (d, 2H, Fmoc), 4.22-3.10 (5m, 14H, 7H from mannitol-CH, 1H from Fmoc, CH$_2$OP, CH$_2$N, CH (iPr)), 3.78 (s, 6H, OCH$_3$), 2.78/2.58 (2t, 2H, CH$_2$CN), 2.35 (m, 1H, mannitol-C-3-H), 2.19 (m, 2H, CH$_2$CO), 1.78-1.27 (2m, 7H, mannitol-C-3-H, CH$_2$ from hexanoyl), 1.06/0.89 (2d, 12H, CH$_3$ (iPr))

$^{31}$P-NMR (CDCl$_3$, in ppm): 150.0/148.3

1.3 Synthesis of Modified Oligonucleotides Using Phosphoramidites

Figure 2:
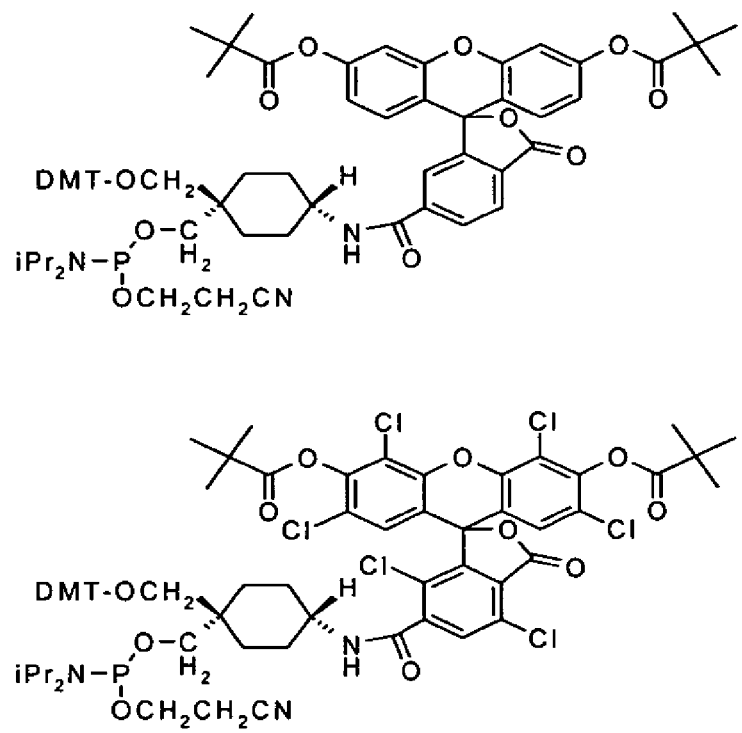
FIG. 2: Labeling reagents FAM- and HEX-cx-phosphoramidite from Biogenex (FAM: fluorescein; HEX: hexachlorofluorescein)

FAM-mannitol-(8) or FAM-glucitol-(15)-phosphoramidites can be incorporated into oligonucleotides applying automated oligonucleotide synthesis and using the phosphoramidite approach and compared to e.g. the FAM-cx-Biogenex-linker (FIG. 2). The different probes can be tested in different formats applying standard methods and perform comparably in terms of background signal, signal gain and c$_T$ value e.g. in the TaqMan® format.

1.4 Synthesis of Modified Oligonucleotides Using Postlabelling

Figure 3:
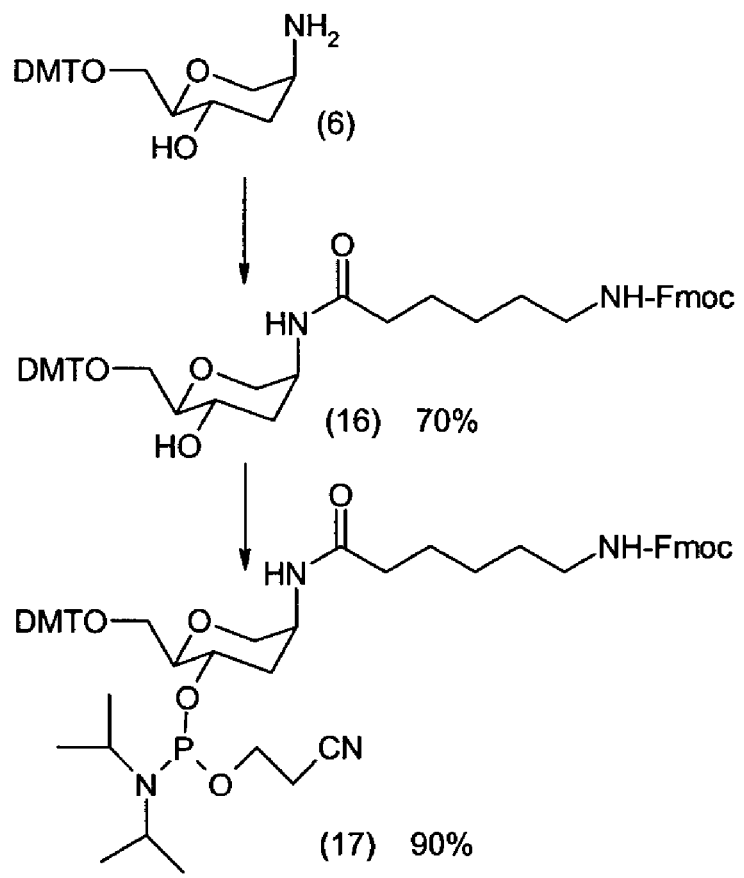
FIG. 3: Synthesis of 6-O-DMT-1,5-anhydro-2,3-dideoxy-2-(N-Fmoc-6-aminocaproylamido)-D-mannitol-4-phosphoramidite (17).

To have the opportunity to incorporate labels postsynthetically an 6-aminocaproyl linking moiety protected by Fmoc was coupled to the mannitol building block 6, subsequently, intermediate 16 was transformed to the corresponding 6-O-DMT-1,5-anhydro-2,3-dideoxy-2-(N-Fmoc-6-aminocaproylamido)-D-mannitol-4-phosphoramidite (17) in excellent yields applying analogous reaction conditions as described above (1.2.15 and 1.2.16) (FIG. 3). Compound 17 was characterized by $^1$H-NMR, $^{31}$P-NMR and HPLC. Monomer 17 could be incorporated into oligonucleotides with high coupling yields. After cleavage from the synthesis support and deprotection several labels (coumarines, rhodamines, cyanines, etc.) were successfully incorporated.

1.5 Hybridization Experiments with Modified Oligonucleotides

The oligonucleotides and modified oligonucleotides disclosed in FIG. 4 were synthesized as described above (1.3) and tested for their hybridization behaviour in PCR-buffer (50 mM Tris, 3 mM magnesium chloride) by determining the melting temperature with standard methods. Determination of the melting temperature was performed on an Uvikon 931 photometer, Kontron Instruments, at 260 nm. Final concentration of each oligonucleotide strand in the Tm buffer was 1 µM. Temperature profile: 15° C.-95° C. within 160 min (heating and cooling); ramp time: 0,5° C./min. It can be seen that the modified oligonucleotides retain the ability to hybridize to complementary oligonucleotides (see FIG. 4).

---

The invention claimed is:
1. A compound of the formula I,

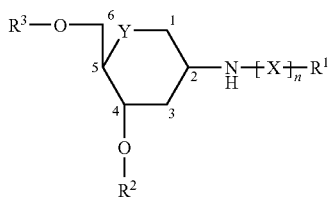

(Formula I)

wherein Y is selected from the group consisting of O, S, and NR$^4$, whereby R$^4$ is alkyl-, alkenyl, alkinyl, aryl-, acyl-, a protecting group or H,
wherein X is a linking moiety in which n is 0 or 1,
wherein R$^1$ is independent from R$^2$, R$^3$ and R$^4$, and wherein R$^1$ is selected from the group consisting of
(1) a protecting group,
(2) a label, and
(3) a solid phase,
wherein R$^2$ and R$^3$ are independent from each other and independent from R$^1$ or R$^4$, and wherein R$^2$ and R$^3$ are selected from the group consisting of
(1) —H,
(2) a protecting group,
(3) a solid phase and a linking moiety X,
(4) a phosphoramidite,
(5) a H-phosphonate, and
(6) a triphosphate,
with the proviso that R$^3$ but not R$^2$ can be triphosphate and R$^1$ is not a solid phase if R$^3$ is a triphosphate,
with the proviso that R$^2$ and R$^3$ are not both a solid phase, not both a phosphoramidite, not both a H-phosphonate, not both —H or not both a protecting group, or not a phosphoramidite and a H-phosphonate, or not a solid phase and a phosphoramidite, or not a solid phase and a H-phosphonate,
and with the proviso that when one residue selected from the group consisting of R$^1$, R$^2$ or R$^3$ is a solid phase then the other two residues selected from the group consisting of R$^1$, R$^2$ or R$^3$ are not a solid phase.

2. A compound according to claim 1, wherein the linking moiety X comprises carbon and oxygen atoms.
3. A compound according to claim 1, wherein the linking Moiety X comprises —(CH$_2$)$_m$ or —(CH$_2$CH$_2$O)$_m$ moieties, whereby m is an integer number between 1 and 10.
4. A compound according to claim 1, wherein the linking moiety X is selected from the group consisting of
(1) —CO—(CH$_2$)$_m$-Z-
(2) —CO—(CH$_2$CH$_2$O)$_m$—CH$_2$CH$_2$-Z-
whereby m is an integer number between 0 and 10 and whereby Z is selected from the group consisting of NH, CO, O and S.
5. A compound according to claim 4, wherein Y is O.
6. A compound according to claim 1, wherein the protecting group is selected from the group consisting of
(1) fluorenylmethoxycarbonyl-,
(2) dimethoxytrityl-,
(3) monomethoxytrityl-,
(4) trifluoroacetyl-,
(5) levulinyl-, and
(6) silyl-.
7. A compound according to claim 1, wherein the label is selected from the group consisting of (1) a fluorescein dye, (2) a rhodamine dye, (3) a cyanine dye, and (4) a coumarin dye.
8. A compound according to claim 1, wherein the compound is a derivative of 1,5-anhydro-2-amino-2,3-dideoxy-D-mannitol or 1,5-anhydro-2-amino-2,3-dideoxy-D-glucitol.
9. An oligomeric compound comprising a monomeric unit of formula II:

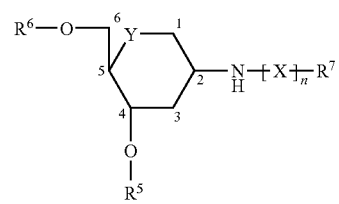

(formula II)

wherein Y is selected from the group consisting of O, S and NR$^4$,
whereby R$^4$ is alkyl-, alkenyl, alkinyl, aryl-, acyl-, a protecting group or H;
wherein X is a linking moiety in which n is 0 or 1,
wherein R$^7$ is independent from R$^4$, R$^5$ and R$^6$ and wherein R$^7$ selected from the group consisting of
(1)—H,
(2) a protecting group,
(3) a label,
(4) an oligonucleotide, and
(5) a solid phase,
wherein R$^5$ and R$^6$ are independent from each other and independent from R$^4$ or R$^7$,
and wherein R$^5$ and R$^6$ are selected from the group consisting of
(1) —H,
(2) a solid phase and a linking moiety X,
(3) a phosphate, and
(4) a phosphodiester with a nucleotide, a modified nucleotide, an oligonucleotide or a modified oligonucleotide,
with the proviso that R$^5$ and R$^6$ are not both —H, both a solid phase and a linking moiety X, both a phosphate, or —H and a phosphate,
with the proviso that when one residue selected from the group consisting of R$^5$, R$^6$ and R$^7$ is a solid phase then the other residues selected from the group consisting of R$^5$, R$^6$ and R$^7$ are not a solid phase.

10. The oligomeric compound according to claim 9, wherein the linking moiety X comprises carbon and oxygen atoms.
11. The oligomeric compound according to claim 9, wherein the linking moiety X comprises —(CH$_2$)$_m$ or —(CH$_2$CH$_2$O)$_m$ moieties in which m is an integer number between 1 and 10.
12. The oligomeric compound according to claim 9, wherein the linking moiety X is selected from the group consisting of
(5) —CO—(CH$_2$)$_m$-Z-
(6) —CO—(CH$_2$CH$_2$O)$_m$—CH$_2$CH$_2$-Z-
whereby m is an integer number between 0 and 10 and whereby Z is selected from the group consisting of NH, CO, O and S.
13. The oligomeric compound according to claim 12, wherein Z is NH and Y is O.

14. The oligomeric compound according to claim 9, wherein the protecting group is selected from the group consisting of
  (1) fluorenylmethoxycarbonyl-,
  (2) dimethoxytrityl-,
  (3) monomethoxytrityl-,
  (4) trifluoroacetyl-,
  (5) levulinyl-, and
  (6) silyl-.

15. The oligomeric compound according to claim 9 wherein the label is a fluorescent label.

16. The oligomeric compound according to claim 9, wherein the modified oligonucleotide comprises a monomeric unit that is
  (1) a linking moiety with a second label attached to a nucleotide, or
  (2) a linking moiety with a second label attached to a modified nucleotide or a non-nucleotide compound.

17. The oligomeric compound according to claim 16, wherein the second label is a second fluorescent label.

18. The oligomeric compound according to claim 15, wherein the fluorescent label is selected from the group consisting of
  (1) a fluorescein dye,
  (2) a rhodamine dye,
  (3) a cyanine dye, and
  (4) a coumarin dye.

19. The oligomeric compound according to claim 9, wherein the oligomeric compound cannot be extended enzymatically.

20. The oligomeric compound according to claim 19, wherein the monomeric unit at the 3'-end of the oligomeric compound is a 2',3'-dideoxy-nucleotide or a 3'-phosphorylated nucleotide.

21. A method for the chemical synthesis of an oligomeric compound according to claim 9, comprising:
  (a) providing a compound of claim 1, wherein $R^2$ is phosphoramidite and $R^3$ is a protecting group,
  (b) providing a 5'-OH group of a nucleoside or a modified nucleoside bound to a solid phase by the 3'-OH group, or providing a 5'-OH group of an oligonucleotide or a modified oligonucleotide bound to a solid phase by the 3'—OH group of the nucleotide or the modified nucleotide at the 3' end of the oligonucleotide or the modified oligonucleotide,
  (c) reacting the phosphorous atom of the phosphoramidite with the 5'—OH group to form a phosphite ester and oxidizing the phosphite ester to a phosphotriester,
  (d) optionally reacting any unreacted 5'—OH group of step (c) with another compound to prevent any further reactions of the unreacted 5'—OH group of step (c) in the following steps,
  (e) optionally repeating steps (a) to (d) with phosphoramidite derivatives of nucleosides or modified nucleosides after removal of the protecting group of the compound of claim 1, and
  (f) cleaving the oligomeric compound from the solid phase, removing the protecting groups and thereby converting the phosphotriester to a phosphodiester, and
  (g) isolating the oligomeric compound.

22. A method for the enzymatic synthesis of a polymeric compound or an oligomeric compound according to claim 9, comprising:
  (a) incubating a compound of claim 1, wherein $R^3$ of said compound is a triphosphate, with a 3'—OH group of the nucleotide or modified nucleotide at the 3'- end of a polynucleotide, oligonucleotide or a modified oligonucleotide in the presence of terminal transferase, whereby the compound is attached to the 3'—OH, and whereby pyrophosphate is released, and
  (b) isolating the polymeric or oligomeric compound.

23. A method to attach a label to an oligomeric compound of claim 9, whereby $R^7$ of the oligomeric compound is a protecting group, comprising:
  (a) removing the protecting group $R^7$, and
  (b) reacting the deprotected moiety of the oligomeric compound with the label.

24. A method for the detection of a target nucleic acid in a sample comprising:
  (a) providing a sample suspected to contain the target nucleic acid,
  (b) providing an oligomeric compound according to claim 9, which is essentially complementary to a part or all of the target nucleic acid,
  (c) optionally amplifying the target nucleic acid with a template-dependent DNA polymerase and primers,
  (d) contacting the sample with the oligomeric compound under conditions for binding the oligomeric compound to the target nucleic acid, and
  (e) determining the binding product or the degree of hybridization between the target nucleic acid and the oligomeric compound as a measure of the presence, absence or amount of the target nucleic acid.

25. The method according to claim 24, wherein the oligomeric compound has a protecting group that is a fluorescent label.

26. The method according to claim 24, wherein in step (d) the degree of hybridization is determined by the quantity of the first or second fluorescent label that is released from the oligomeric compound hybridized to the target nucleic acid by exonuclease hydrolysis by the template-dependent DNA polymerase.

27. A method for detecting the presence or absence of a target nucleic acid in a sample, comprising:
  performing at least one cycling step, wherein a cycling step comprises an amplifying step and a hybridizing step, wherein said amplifying step comprises contacting said sample with primers to produce a an amplification product if target nucleic acid is present in said sample, wherein said hybridizing step comprises contacting said sample with a pair of probes, wherein at least one of the probes is an oligomeric compound according to claim 9 wherein $R^7$ is a label, wherein the members of said pair of probes hybridize to said amplification product within no more than five nucleotides of each other, wherein a first probe of said pair of probes is labeled with a donor fluorescent label and wherein a second probe of said pair of probes is labeled with an acceptor fluorescent label;
  and detecting the presence or absence of fluorescence resonance energy transfer between said donor fluorescent label of said first probe and said acceptor fluorescent label of said second probe, wherein the presence of fluorescence resonance energy transfer is indicative of the presence of the target nucleic acid in the sample, and wherein the absence of fluorescence resonance energy transfer is indicative of the absence of the target nucleic acid in the sample.

28. A kit for detecting a target nucleic acid in a sample, comprising:
  a template-dependent polymerase having 3' to 5' exonucleolytic activity,
  a set of primers,
  nucleotides, and
  an oligomeric compound according to claim 9, wherein $R^7$ is a label.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 1
caccccgtgc tgctgaccga                                            20

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 2
```

```
gggcctcggt cagcagcacg gggtg                                              25

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:
      oligonucleotide
<220> FEATURE:
<223> OTHER INFORMATION: N in position 21 denotes FAM-Mannitol compound
      according to the invention, whereby FAM stands for
      fluorescein attached via a linking moiety to the
      mannitol moiety

<400> SEQUENCE: 3 cacccgtgc tgctgaccga n                                                   21

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
gggcctcggt cagcagcacg gggtg                                              25

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:
      oligonucleotide
<220> FEATURE:
<223> OTHER INFORMATION: N in position 11 denotes FAM-Mannitol compound
      according to the invention, whereby FAM stands for
      fluorescein attached via a linking moiety to the
      mannitol moiety

<400> SEQUENCE: 5 cacccgtgc ngctgaccga                                                     20

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
gggcctcggt cagcagcacg gggtg                                              25
```